US010015971B2

(12) United States Patent
Allen et al.

(10) Patent No.: US 10,015,971 B2
(45) Date of Patent: *Jul. 10, 2018

(54) ARTICLES AND METHODS FOR ADMINISTERING $CO_2$ INTO PLANTS

(71) Applicant: Elwha LLC, Bellevue, WA (US)

(72) Inventors: Paul G. Allen, Mercer Island, WA (US); Kenneth G. Caldeira, Redwood City, CA (US); Bran Ferren, Beverly Hills, CA (US); William Gates, Medina, WA (US); W. Daniel Hillis, Encino, CA (US); Roderick A. Hyde, Redmond, WA (US); Muriel Y. Ishikawa, Livermore, CA (US); Edward K. Y. Jung, Bellevue, WA (US); Jordin T. Kare, Seattle, WA (US); John Latham, Boulder, CO (US); Nathan P. Myhrvold, Medina, WA (US); Stephen H. Salter, Edinburgh (GB); Clarence T. Tegreene, Mercer Island, WA (US); David B. Tuckerman, Lafayette, CA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,095

(22) Filed: Dec. 28, 2012

(65) Prior Publication Data

US 2014/0187425 A1 Jul. 3, 2014

(51) Int. Cl.
*A01N 59/04* (2006.01)
*A01G 7/02* (2006.01)
*A01N 37/36* (2006.01)
*A01N 43/16* (2006.01)
*C10B 53/02* (2006.01)

(52) U.S. Cl.
CPC .............. *A01N 59/04* (2013.01); *A01G 7/02* (2013.01); *A01N 37/36* (2013.01); *A01N 43/16* (2013.01); *C01B 2203/86* (2013.01); *C10B 53/02* (2013.01); *Y02P 60/24* (2015.11)

(58) Field of Classification Search
None
See application file for complete search history.

(56) References Cited

U.S. PATENT DOCUMENTS

| | | | |
|---|---|---|---|
| 2,044,063 A | 6/1936 | Dahlberg | |
| 3,539,373 A * | 11/1970 | Cooke | 427/4 |
| 3,673,733 A * | 7/1972 | Allen | 47/17 |
| 3,826,671 A * | 7/1974 | Petrucco et al. | A01N 61/00 47/58.1 R |
| 4,011,685 A | 3/1977 | Boyd et al. | |
| 4,056,899 A | 11/1977 | Close | |
| 4,624,193 A * | 11/1986 | Johnston | 111/127 |
| 4,651,468 A | 3/1987 | Martinez et al. | |
| 4,666,849 A | 5/1987 | Daeschel et al. | |
| 4,706,645 A | 11/1987 | Ostlie | |
| 5,171,301 A | 12/1992 | Vanderveen | |
| 5,225,342 A | 7/1993 | Farrell | |
| 5,522,798 A | 6/1996 | Johnson et al. | |
| 5,665,070 A | 9/1997 | McPhee | |
| 5,743,878 A | 4/1998 | Ross et al. | |
| 6,108,967 A | 8/2000 | Erickson | |
| 6,213,738 B1 | 4/2001 | Danby et al. | |
| 6,237,284 B1 * | 5/2001 | Erickson | A01G 7/02 47/1.5 |
| 6,270,478 B1 | 8/2001 | Mernoe | |
| 6,405,480 B1 | 6/2002 | Martin | |
| 6,407,040 B1 * | 6/2002 | Nichols | 504/140 |
| 6,669,668 B1 | 12/2003 | Kleeman et al. | |
| 7,966,767 B2 | 6/2011 | Perriello et al. | |
| 2002/0046486 A1 | 4/2002 | Wild et al. | |
| 2003/0005626 A1 | 1/2003 | Yoneda et al. | |
| 2003/0084609 A1 | 5/2003 | Perriello et al. | |
| 2005/0000154 A1 | 1/2005 | Perriello et al. | |
| 2006/0015967 A1 | 1/2006 | Boerjan et al. | |
| 2009/0307970 A1 * | 12/2009 | Holman | A01H 3/00 47/17 |
| 2010/0196742 A1 | 8/2010 | Nealson et al. | |
| 2010/0218507 A1 * | 9/2010 | Cherson | C01B 3/12 60/780 |
| 2011/0011945 A1 | 1/2011 | Eisenberger et al. | |
| 2011/0083554 A1 | 4/2011 | Wright et al. | |
| 2011/0270531 A1 | 11/2011 | Moshelion et al. | |

FOREIGN PATENT DOCUMENTS

| | | |
|---|---|---|
| JP | 10295207 A | 11/1998 |
| JP | 2004-239187 A | 8/2004 |
| JP | 2008-258029 A | 10/2008 |
| KR | 10-1063372 B1 | 9/2011 |
| WO | WO 00/22101 A2 | 4/2000 |
| WO | WO 2008/070280 A2 * | 6/2008 |

OTHER PUBLICATIONS

Article for Fungicide Terminology, obtained online via http://www.ipm.iastate.edu/ipm/icm/2006/5-15/fungicides.html (printed on Mar. 13, 2014).*

(Continued)

*Primary Examiner* — Mina Haghighatian
*Assistant Examiner* — Mei Ping Chui
(74) *Attorney, Agent, or Firm* — Foley & Lardner LLP

(57) ABSTRACT

Methods and articles are provided for reducing the amount of water consumed by a plant over a period of time, sequestering $CO_2$, and producing electricity, where each method includes providing the plant with a composition including at least about 0.1 (wt./wt. or vol./vol.) % $CO_2$ and/or at least about 0.1 wt./wt. % of a composition that generates $CO_2$. An apparatus is also disclosed for providing the plant with a composition including $CO_2$ and/or a composition that generates $CO_2$.

23 Claims, 8 Drawing Sheets

(56) References Cited

OTHER PUBLICATIONS

Definition for Excipient (obtained online via http://en.wikipedia.org, printed on Mar. 13, 2014).*
PCT International Search Report; International App. No. PCT/US2013/076103; dated Apr. 7, 2014; pp. 1-3.
PCT International Search Report; International App. No. PCT/US2013/076094; dated Apr. 7, 2014; pp. 1-5.
Enoch et al.; "Effect of Light Intensity, Carbon Dioxide Concentration, and Leaf Temperature on Gas Exchange of Spray Carnation Plants"; Journal of Experimental Botany; Feb. 1977; pp. 84-95; vol. 28, No. 102.
Fletcher et al.; "Atmospheric carbon dioxide linked with Mesozoic and early Cenozoic climate change"; Nature Geoscience; Jan. 2008; pp. 43-48; vol. 1; Nature Publishing Group.
Giora et al; "Reproduction and Feeding of the Electric Fish *Brachyhypopomus gauderio* (Gymnotiformes: Hypopomidae) and the Discussion of a Life History Pattern for Gymnotiforms from High Latitudes"; PLOS ONE; Sep. 2014; pp. 1-11; vol. 9, Issue 9; available at www.plosone.org.
Jenkins et al.; "Form of Inorganic Carbon Involved as a Product and as an Inhibitor of $C_4$ Acid Decarboxylases Operating in $C_4$ Photosynthesis"; Plant Physiol.; bearing a date of Jul. 16, 1987; pp. 952-957; vol. 85.
Kaku et al.; "Plant/microbe cooperation for electricity generation in a rice paddy field"; Appl Microbiol Biotechnol; bearing a date of Mar. 5, 2008; pp. 43-49; vol. 79; Springer-Verlag.
Long et al.; "Rising Atmospheric Carbon Dioxide: Plants FACE the Future"; Annual Review of Plant Biology; bearing a date of 2004; pp. 591-628 and Figures 1, 4 and 5; vol. 55; available at http://plant.annualreviews.org.
March, Jerry; "The Decarboxylation of Organic Acids"; Journal of Chemical Education; bearing a date of Apr. 1963; pp. 212-213; vol. 40, No. 4.
Merriam-Webster; definition of "excipient"; retrieved on Oct. 20, 2014; 1 page; located at http://www.merriam-webster.com/dictionary/excipient.
Peng et al.; "Mitochondrial molecular clocks and the origin of the major Otocephalan clades (Pisces: Teleostei): A new insight"; GENE Section Evolutionary Genomics; bearing a date of 2006; pp. 113-124; vol. 370; Elsevier B.V.
Pilone et al.; "Carbonic Acid from Decarboxylation by 'Mahe' Enzyme in Lactic Acid Bacteria"; Journal of Bacteriology; Aug. 1970; pp. 404-409; vol. 103, No. 2; American Society for Microbiology.
Pitt et al.; "Testing Citric Acid Use on Plants"; USDA National Wildlife Research Center—Staff Publications, Paper 377; Jul.-Aug. 2004; 3 pages; Internet Center for Wildlife Damage Management.
Strik et al.; "Short Communication Green electricity production with living plants and bacteria in a fuel cell"; International Journal of Energy Research; bearing a date of Nov. 23, 2007; pp. 870-876; vol. 32; John Wiley & Sons, Ltd.
Vines et al.; "Some Effects of Ammonia on Plant Metabolism and a Possible Mechanism for Ammonia Toxicity"; Department of Plant Biochemistry, University of California Citrus Experiment Station, Riverside; bearing a date of Mar. 19, 1960; pp. 820-825; American Society of Plant Biologists; available at www.plant.org.
Cushman et al., "Large-scale mRNA expression profiling in the common ice plant, Mesembryanthemum crystallinum, performing C3 photosynthesis and Crassulacean acid metabolism (CAM)", Journal of Experimental Botany, 2008, vol. 59, No. 7, pp. 1875-1894.

Cushman, John C., "Crassulacean Acid Metabolism. A Plastic Photosynthetic Adaptation to Arid Environments" Plant Physiology, Dec. 2001, vol. 127, pp. 1439-1448.
G.T. Rochelle et al., "Amine Scrubbing for CO2 Capture," Science, Sep. 25, 2009, pp. 1652-1654.
H. Dang and G.T. Rochelle, "CO2 Absorption Rate and Solubility in Monoethanolamine/Piperazine/Water", given at the First National Conference on Carbon Sequestration, Washington, DC, May 14-17, 2001, 17 pages.
Haider MS et al., "A CAM- and starch-deficient mutant of the facultative CAM species Mesembryanthemum crystallinum reconciles sink demands by repartitioning carbon during acclimation to salinity" Journal of Experimental Botany, vol. 63, No. 5, pp. 1985-1996, Mar. 2012.
Mallona et al., "Conserved and Divergent Rhythms of Crassulacean Acid Metabolism-Related and Core Clock Gene Expression in the Cactus Opuntia ficus-Indica", Plant Physiology, Aug. 2011, vol. 156, No. 4, pp. 1978-1989.
Xing et al., "Disruption of the 1-deoxy-D-xylulose-5-phosphate reductoisomerase (DXR) gene results in albino, dwarf and defects in trichome initiation and stomata closure in *Arabidopsis*", Cell Research, 2010, vol. 20, pp. 688-700.
Amri et al.; Comparative Efficacy of Citric Acid and Fe(II) Sulfate in the Prevention of Chlorosis in Orange Trees (*Citrus sinesis* L. cv 'Darabi'); J. Biol. Envron., Sci.; bearing a date of 2009, printed on Jul. 23, 2015; pp. 61-65; vol. 3(8).
Definition from Meriam-Webster; "extract"; Merriam-Webster Online Dictionary; cited and printed by examiner on Apr. 30, 2015; pp. 1-4 (as provided by examiner); located at: www.merriam-webster.com/dictionary/extract.
Finkemeier et al.; "The role of malate in plant homeostasis"; F1000 Biology Reports; Jun. 29, 2009; pp. 1-3; vol. No. 1:47; 2009 Biology Reports Ltd.; located at: http://F1000.com/Reports/_Biology/content/1/47.
Jafari et al.; "Growth and Essential Oil Yield of Dill (*Anethum graveolens*) As Affected by Foliar Sprays of Critic Acid and Malic Acid"; ISHS Acta-Horticulturae 955: | International Symposium on Medicinal, Aromatic and Nutraceutical Plants from Mountainous Areas (MAP-Mountain 2011); bearing a date of 2012, printed on Apr. 20, 2015; pp. 287-290 plus Abstract; located at: http://www.actahort.org/books/955/955_42.htm.
Paoletti et al.; "Modifications of the leaf surface structures of *Quercus ilex* L. in naturally CO2-enriched environments"; Plant, Cell and Environment; bearing a date of Jun. 22, 1998; pp. 1071-1075; vol. 21; Blackwell Science Ltd.
Aarrestad et al.; "Effects on Terrestrial Vegetation, Soil and Fauna of Amines and Possible Degradation Products Relevant for CO2 Capture"; NILU Task 8 Report; Feb. 2009; pp. 1-29.
Apblett et al.; "Small Scale Bio Fuel Cells for Long Duration Unattended Ground Sensor Applications"; The Sixth International Workshop on Micro and Nanotechnology for Power Generation and Energy Conversion Applications; Nov. 29-Dec. 1, 2006; pp. 271-274.
"Carbon dioxide scrubber"; Wikipedia; bearing a date of Aug. 23, 2015; printed on Nov. 6, 2015; pp. 1-5; located at: https://en.wikipedia.org/wiki/Carbon_dioxide_scrubber.
"'Juiced-up' Sugar-Fueled Battery Could Power Portable Electronics"; phys.org; bearing a date of Mar. 25, 2007; printed on Aug. 19, 2015; pp. 1-2; located at: http://phys.org/news/2007-03-juiced-up-sugar-fueled-battery-power-portable.html.
Mikkelsen et al.; "The teraton challenge. A review of fixation and transformation of carbon dioxide"; Energy Environ. Sci.; Nov. 24, 2009; pp. 43-81; vol. 3; The Royal Society of Chemistry.

* cited by examiner

ARTICLES AND METHODS FOR ADMINISTERING CO₂ INTO PLANTS

CROSS-REFERENCE TO RELATED PATENT APPLICATIONS

This application is related to U.S. patent application Ser. Nos. 13/729,082 and 13/729,089, both entitled "Articles and Methods for Administering $CO_2$ Into Plants," filed on Dec. 28, 2012, and both incorporated herein by reference in their entireties.

BACKGROUND

The present technology relates generally to the administration of carbon dioxide into plants such as trees.

Demand for staple commodities such as fresh water and energy has grown with the increasing human population and as the supply of inexpensive water and energy has declined. It has been postulated that the increased demand has impacted the environment, for example, by increasing the concentration of atmospheric $CO_2$ upon the consumption of fossil fuels.

Regarding fresh water supplies, there is a significant interest in conserving the amount of water that is consumed by plants. For example, a large fully grown tree may evaporate, or "transpire," several hundred gallons of water through its leaves on a hot, dry day. At least ninety percent of the water that enters a plant's roots is used in this process of transpiration. Thus, methods for decreasing the rate of transpiration of plants, such as trees, would serve to conserve fresh water supplies, especially usefully in arid regions where such supplies are scarce.

Regarding energy supplies, there exists a growing need to identify renewable sources of affordable energy from plants. Most of the existing renewable sources of energy are crop-based that require harvesting or killing the entire plant to convert some of the plant's vegetation product into fuel. Methods for obtaining energy from plants, without harvesting and thus destroying the entire plant, would provide a superior source of renewable energy.

As noted, a consequence of the human population growth is postulated to include an increase in the concentration of atmospheric $CO_2$ from the consumption of increased quantities of carbon-based energy. Effective methods for $CO_2$ sequestration would be useful to stabilize or decelerate such increasing levels of atmospheric $CO_2$.

SUMMARY

The present technology relates generally to articles and methods for providing a plant with a composition including at least about 0.1 (wt./wt. or vol./vol.) % $CO_2$ and/or at least about 0.1 wt./wt. % of a composition that generates $CO_2$. The present technology further provides methods for reducing the amount of water consumed by a plant over a period of time, methods for sequestering $CO_2$, and methods for producing heat or electricity, where each method includes providing the plant with a composition including $CO_2$ and/or a composition that generates $CO_2$.

According to one aspect, a method is provided for reducing the amount of water removed from soil by a plant over an interval of time, including providing the plant with a composition that is at least one of a composition comprising at least about 0.1 (wt./wt. or vol./vol.) % $CO_2$, or at least about 0.1 wt./wt. % of a composition that generates $CO_2$.

According to another aspect, an article is provided where the article includes a plant, and a composition that comprises at least about 0.1 (wt./wt. or vol./vol.) % $CO_2$ or at least about 0.1 wt./wt. % of a composition that generates $CO_2$.

According to yet another aspect, an apparatus is provided for providing a composition that comprises $CO_2$ or a composition that generates $CO_2$ into a plant, where the apparatus includes the following components: at least one infusion pump for delivering the composition that comprises $CO_2$ or the composition that generates $CO_2$ into the plant; at least one sensor; at least one control unit comprising a microprocessor; at least one user interface, operatively connected to the control unit; and at least one data output interface operatively connected to one or more of the other components.

According to an additional aspect, a method is provided for sequestering $CO_2$ comprising providing a plant with a composition that is at least one of a composition comprising at least about 0.1 (wt./wt. or vol./vol.) % $CO_2$ or at least about 0.1 wt./wt. % of a composition that generates $CO_2$; removing carbon-based photosynthate from the plant; and storing or processing the carbon-based photosynthate.

In another aspect, the present technology provides a method for producing electricity comprising: providing a composition, that is at least one of a composition comprising at least about 0.1 (wt./wt. or vol./vol.) % $CO_2$ or at least about 0.1 wt./wt. % of a composition that generates $CO_2$, into a plant; removing a carbon-based photosynthate from the plant; processing at least a fraction of the carbon-based photosynthate to produce energy and a product stream; and converting at least some of the energy into electricity.

In some embodiments, the composition that generates $CO_2$ includes the reaction product of an amine, or a salt thereof, with $CO_2$. In other embodiments, the composition that generates $CO_2$ includes a $CO_2$-precursor compound, or salt thereof, selected from citric acid, cis-aconitic acid, isocitric acid, oxalosuccinic acid, α-ketoglutaric acid, succinic acid, fumaric acid, malic acid, oxaloacetic acid, and a combination thereof.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The skilled artisan will understand that the drawings primarily are for illustrative purposes and are not intended to limit the scope of the inventive subject matter described herein.

DETAILED DESCRIPTION

Figure 1A:
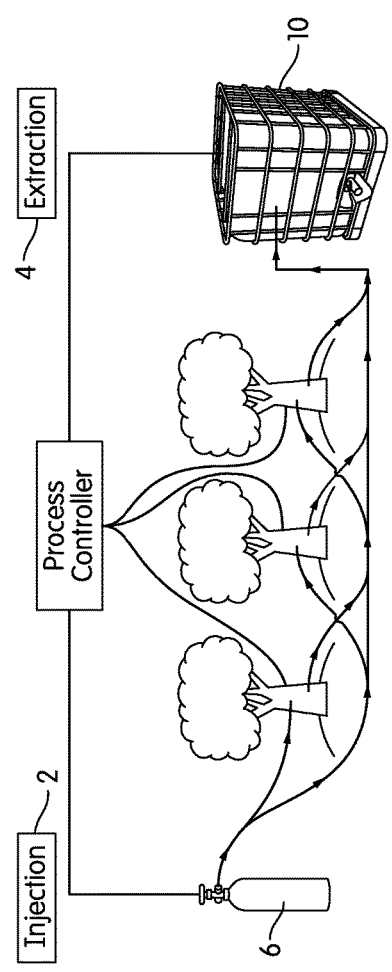
FIG. 1A illustrates an article for sequestering $CO_2$, including an apparatus for providing a plant with a gaseous composition including $CO_2$ and/or a composition that generates $CO_2$, in accordance with one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1B:
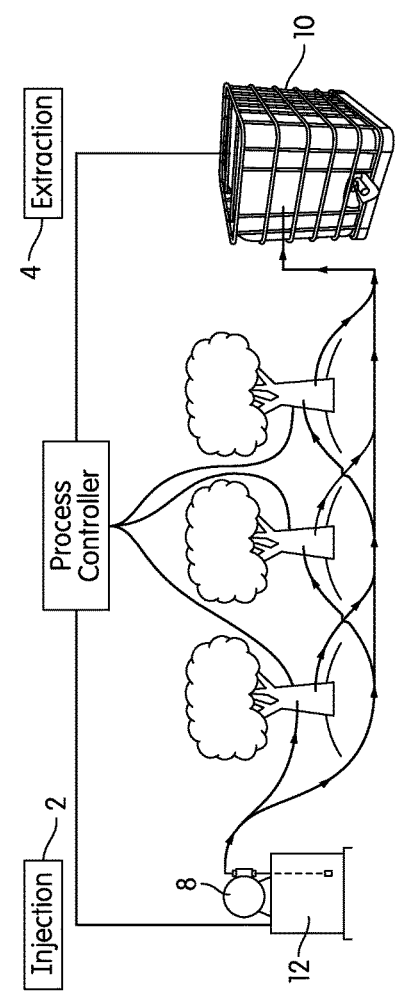
FIG. 1B illustrates an article for sequestering $CO_2$, including an apparatus for providing a plant with a fluid composition including $CO_2$ and/or a composition that generates $CO_2$, in accordance with one embodiment.

Referring to FIGS. 1A-1B, in accordance with two embodiments, articles are shown for sequestering $CO_2$, including an apparatus (shown as a pressurized gas cylinder in 6 in FIG. 1A or a container 12 in FIG. 1B) for providing a plant with a composition including $CO_2$ and/or a composition that generates $CO_2$, and an apparatus 10 for extracting or storing a carbon-based photosynthate. In FIG. 1A, a gaseous composition including $CO_2$ and/or a composition that generates $CO_2$, is provided from a gas container 6. In FIG. 1B, a fluid composition including $CO_2$ and/or a composition that generates $CO_2$, is provided from container 12 having pump 8. A process controller such as a computer can be used to monitor the plants (e.g., temperature, water consumption, etc.) and control the providing and removing steps (e.g., the sourcing and sinking of $CO_2$).

Figure 2:
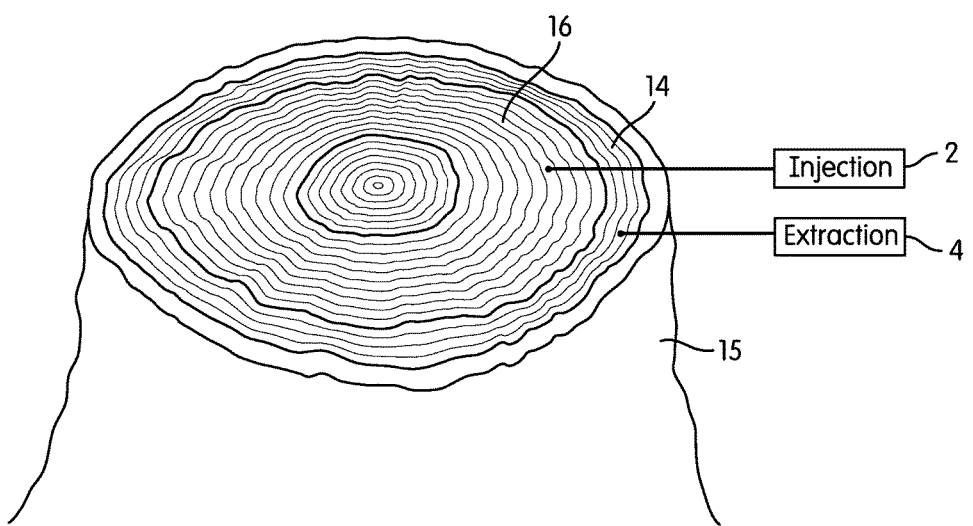
FIG. 2 illustrates regions within a tree into which a fluid composition including $CO_2$ and/or a composition that generates $CO_2$, can be provided, and from which a composition including carbon-based photosynthates can be extracted, in accordance with one embodiment.

Referring to FIG. 2, in accordance with one embodiment, an illustration is provided of regions, such as xylem region 16 of tree 15, into which a fluid composition including $CO_2$ and/or a composition that generates $CO_2$ can be provided by an apparatus 2. Also shown are regions, such as phloem 14, from which a composition including carbon-based photosynthates can be extracted by removal apparatus 4.

Figure 3:
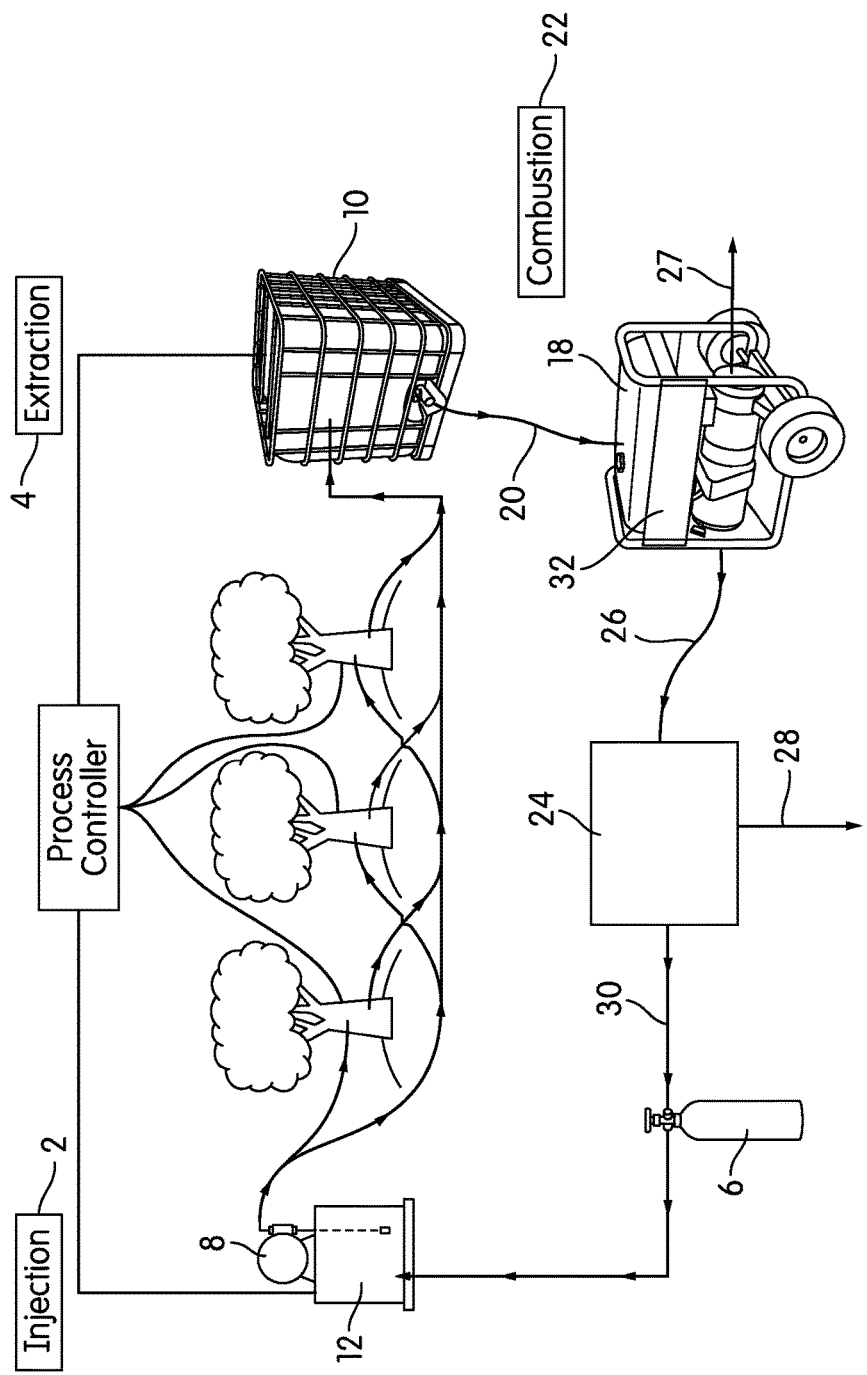
FIG. 3 illustrates a fuel cell, in accordance with one embodiment.

Referring to FIG. 3, a fuel cell is shown according to one embodiment including articles for sequestering $CO_2$, including an apparatus shown as a container 12 having pump 8 for providing a plant with a composition including $CO_2$ and/or a composition that generates $CO_2$ and an apparatus 10 for removing or storing a composition including carbon-based photosynthates. In FIG. 3, the composition including carbon-based photosynthates can be transported via a conduit 20 (e.g., flow line, pipe, tube, hose, etc.) into a tank 18 of generator 32. Electricity from generator 32 is transmitted to another device or system via an output 27. Exhaust from generator 32 can be conducted via an exhaust line 26 to an apparatus 24 for purifying $CO_2$. Substantially pure $CO_2$ can be transported via a conduit 30 (e.g., flow line, pipe, tube, hose, etc.) into a $CO_2$ cylinder 6 and the remaining impurities from the exhaust can be vented via an output 28. The $CO_2$ in tank 6 can be transported to container 12 having pump 8 for providing $CO_2$ into the plant. A process controller such as a computer can be used to monitor the plants (e.g., temperature, water consumption, etc.) and control the providing and removal steps.

Figure 4:
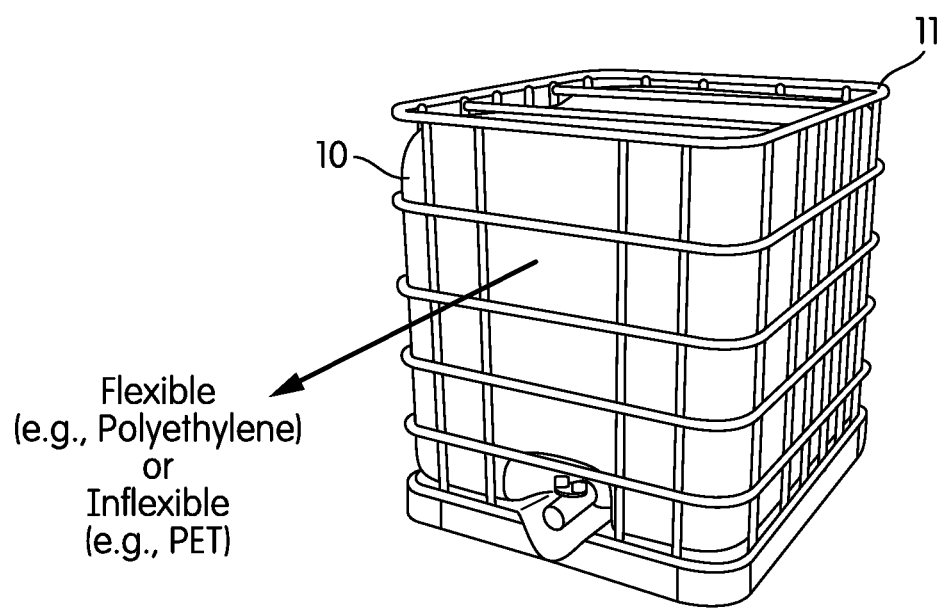
FIG. 4 illustrates a container for storing a composition including carbon-based photosynthates, in accordance with one embodiment.

Referring to FIG. 4, in accordance with one embodiment, an apparatus 10 is shown for extracting or storing a composition including carbon-based photosynthates. Frame 11 provides structural support and a mechanism for lifting and transporting apparatus 10, which can be made of materials, for example, such as stainless steel, aluminum, and flexible (e.g., collapsible) or inflexible plastic, ceramic or glass.

Figure 5:
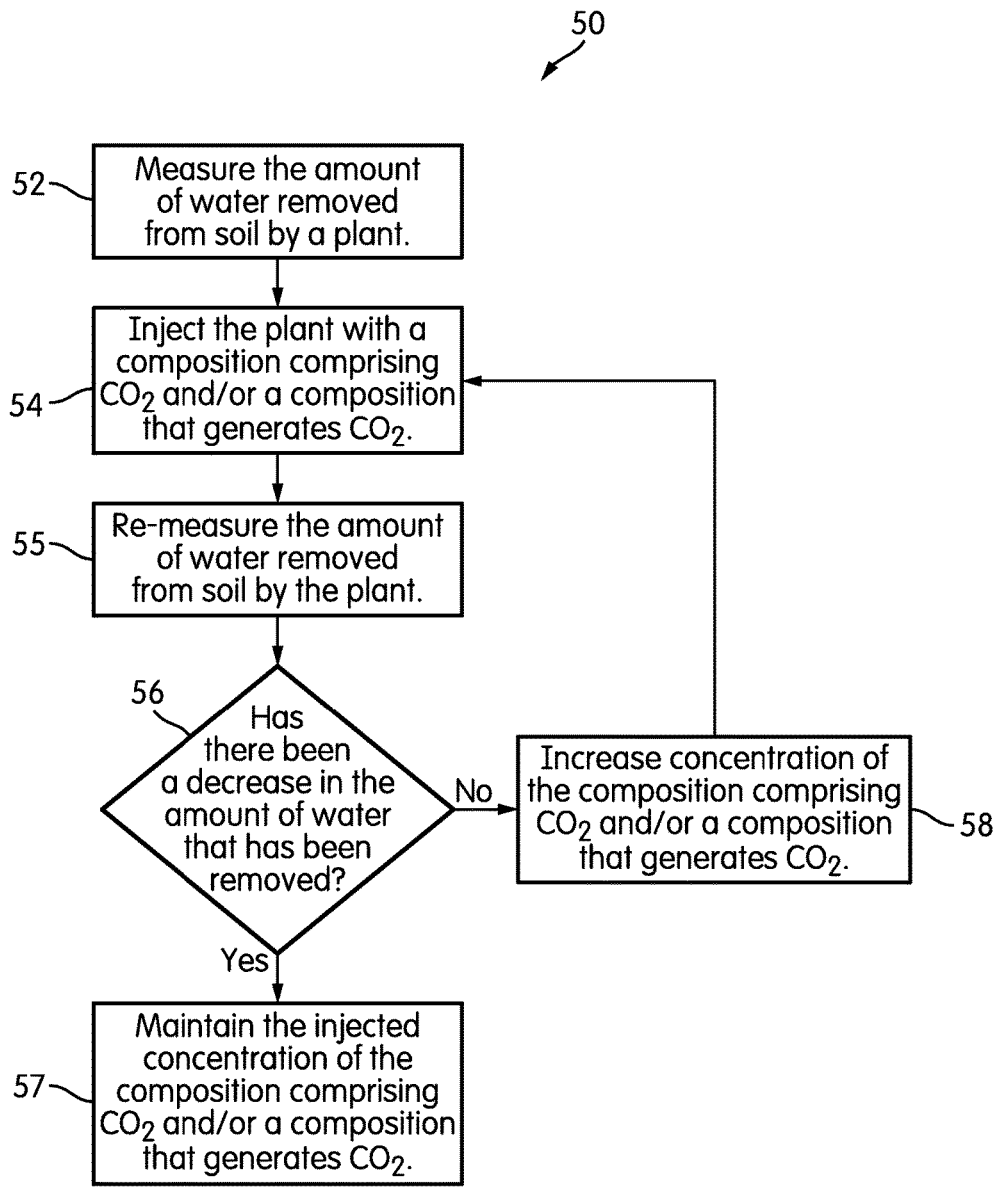
FIG. 5 illustrates a method for reducing the amount of water drawn from the soil by a plant over a period of time, in accordance with one embodiment.
Figure 6:
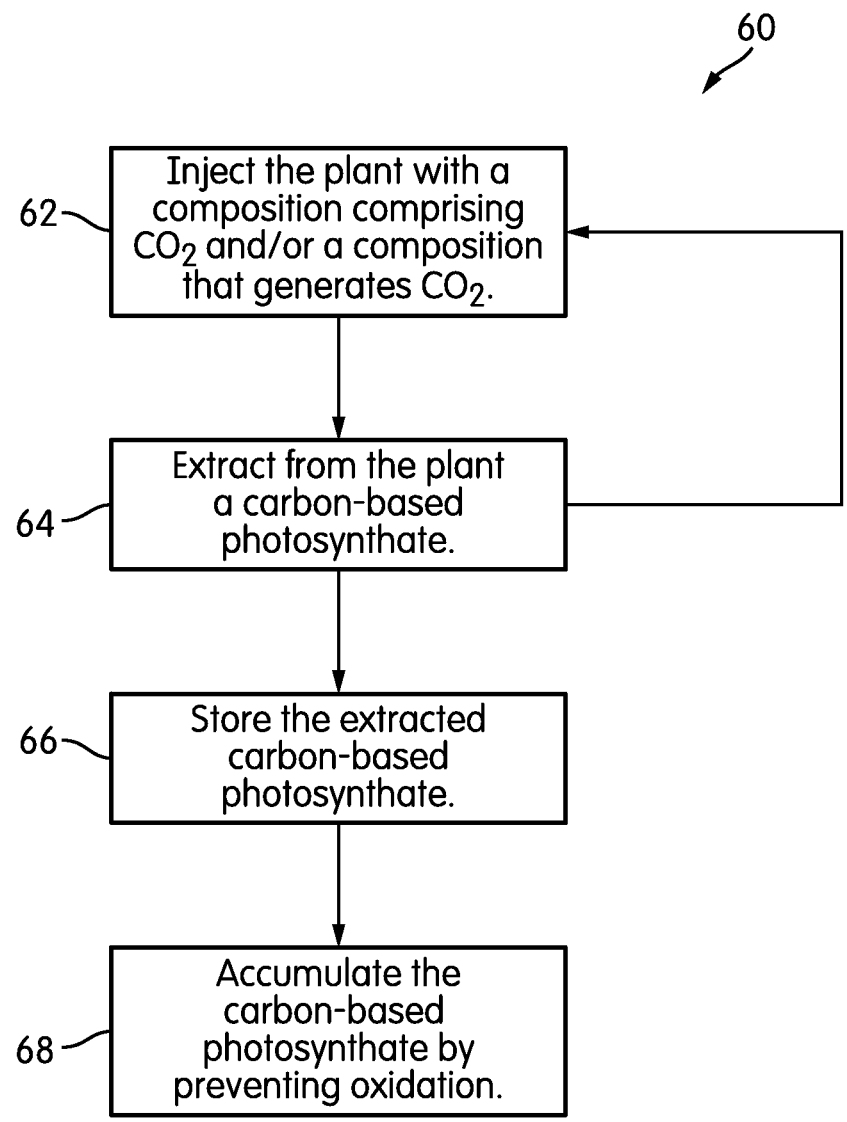
FIG. 6 illustrates a method for sequestering $CO_2$, in accordance with one embodiment.
Figure 7:
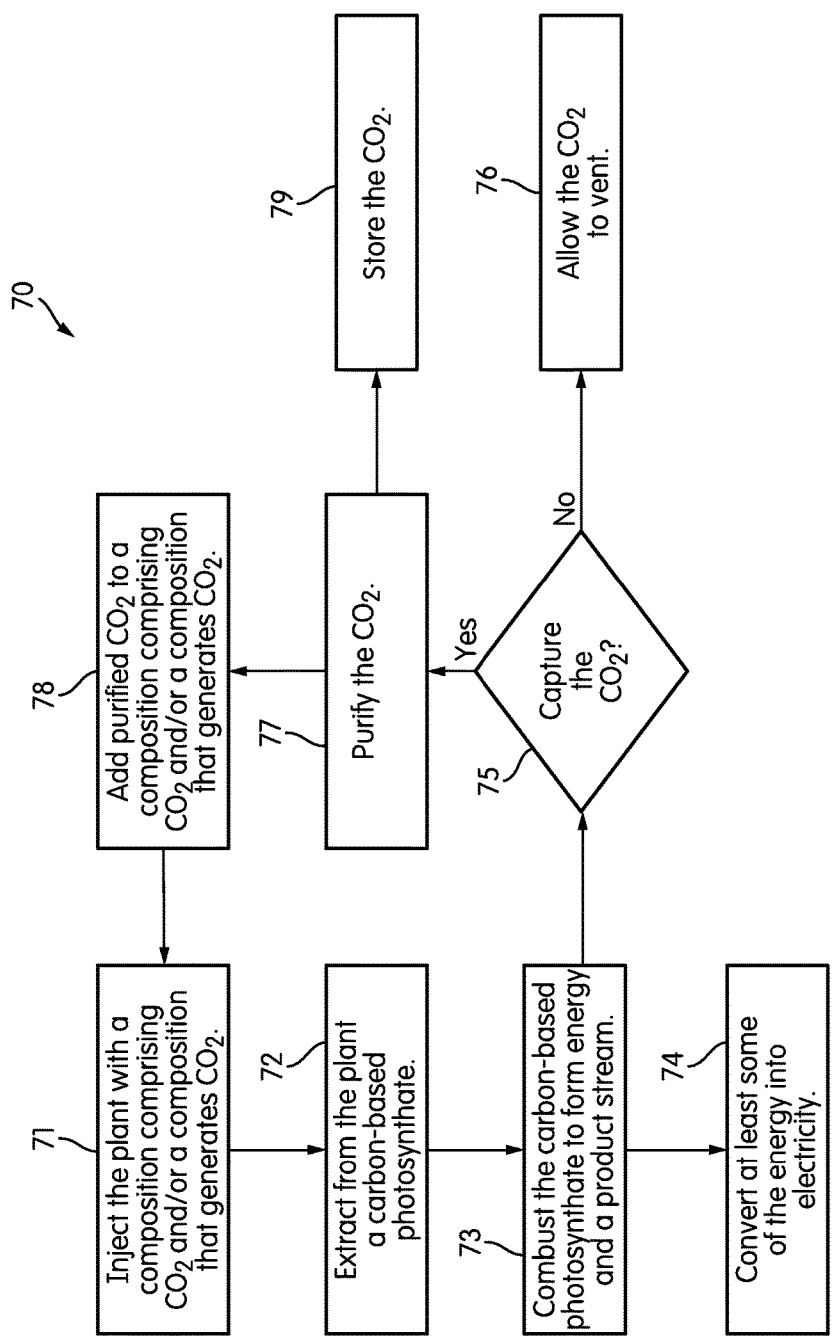
FIG. 7 illustrates a method for producing electricity, in accordance with one embodiment.

Referring generally to FIGS. 5-7, various methods are shown for providing a plant with a composition including $CO_2$ and/or a composition that generates $CO_2$ according to several embodiments.

Referring to FIG. 5, a flowchart depicts process 50 for determining the concentration of the composition including $CO_2$ and/or a composition that generates $CO_2$, and that is provided to a plant, according to one embodiment. The amount of water removed from soil by a plant is measured (step 52). The plant is then provided with a composition including $CO_2$ and/or a composition that generates $CO_2$ (step 54). The amount of water from the soil that is extracted by the plant is re-measured (step 55) and compared to the initial water extraction (step 56). If the re-measurement establishes that the amount of water from the soil that is extracted by the plant has decreased, the provided concentration of the composition including $CO_2$ and/or a composition that generates $CO_2$ is maintained (step 57). If the re-measurement establishes that the amount of water from the soil that is extracted by the plant has increased or not decreased, the concentration of the composition including $CO_2$ and/or a composition that generates $CO_2$ may be increased (step 58). In an embodiment, measurements on water use from a first plant can be used in order to control the amount of a composition including $CO_2$ and/or a composition that generates $CO_2$ which is provided to a second similar plant. For instance, correlations between water usage and $CO_2$-related compositions can be determined from a set of monitored plants, and these correlations can be then used to determine the amount of $CO_2$-related compositions provided to other plants of the same species.

Referring to FIG. 6, a flowchart depicts process 60 for sequestering $CO_2$ according to one embodiment. The plant is provided with a composition including $CO_2$ and/or a composition that generates $CO_2$ (step 62), and a composition including carbon-based photosynthates is extracted from the plant (step 64). The plant may optionally be provided again with a composition including $CO_2$ and/or a composition that generates $CO_2$ (step 62). The removed composition including carbon-based photosynthates is stored (step 66) and the composition including carbon-based photosynthates is accumulated (step 68).

Referring to FIG. 7, a flowchart depicts process 70 for producing electricity according to one embodiment. A composition including $CO_2$ and/or a composition that generates $CO_2$ is provided to the plant (step 71), a composition including carbon-based photosynthates is removed from the plant (step 72), the composition including carbon-based photosynthates is processed to release energy and exhaust (step 73), and at least some of the energy is converted into electricity (step 74). The exhaust may optionally be captured (step 75) or allowed to vent (step 76). If the exhaust is captured, the $CO_2$ is purified from the exhaust (step 77). The purified $CO_2$ may be added to a composition including $CO_2$ and/or a composition that generates $CO_2$ may be stored (step 79).

Figure 8A:
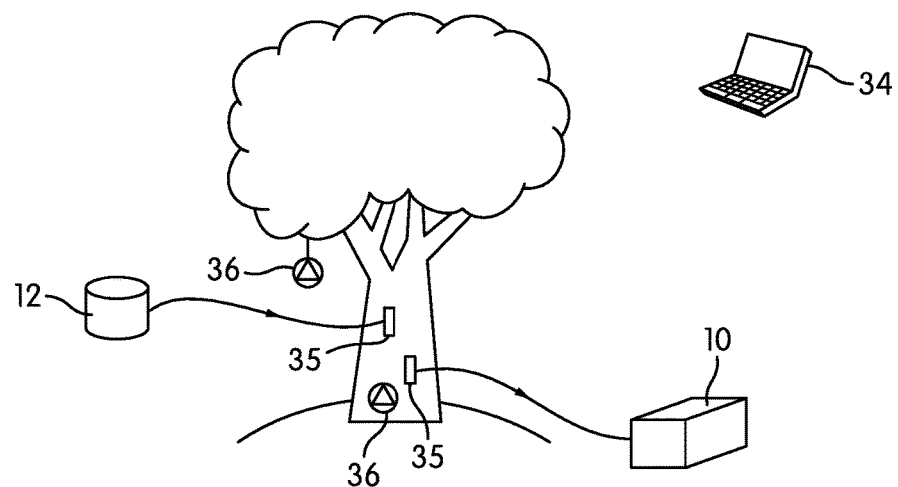
FIG. 8A illustrates an apparatus for providing a composition that comprises $CO_2$ or a composition that generates $CO_2$ into a plant, in accordance with one embodiment.

Referring to FIG. 8A, in accordance with one embodiment, an apparatus is shown for providing into a plant a composition that comprises $CO_2$ or a composition that generates $CO_2$. Container 12 provides into the plant a composition including $CO_2$ and/or a composition that generates $CO_2$, and container 10 stores a carbon-based photosynthate that is extracted from the plant. Pumps 35 are optionally installed within the plant and/or in the proximity of the plant and/or in the proximity of containers 10 and 12 to provide a composition including $CO_2$ and/or a composition that generates $CO_2$, and to extract the carbon-based photosynthate from the plant. Sensors 36 are optionally installed within the plant and/or in the proximity of the plant. In one embodiment, containers 10 and 12, pumps 35, and sensors 36 exchange data with the control unit in a wireless fashion.

Figure 8B:
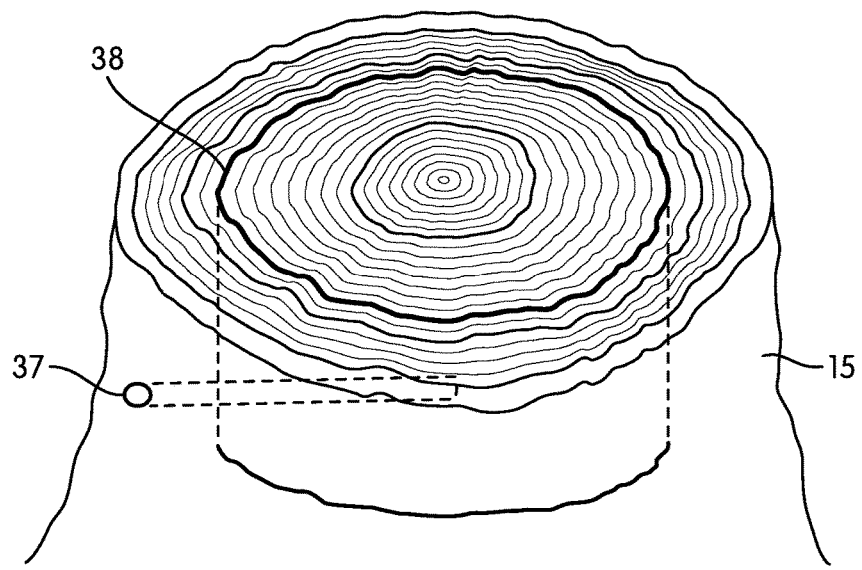
FIG. 8B illustrates interior channels, into which a fluid composition including $CO_2$ and/or a composition that generates $CO_2$ can be provided to a tree, in accordance with one embodiment.

Referring to FIG. 8B, in accordance with one embodiment, an illustration is provided of interior channels 38, into which a fluid composition including $CO_2$ and/or a composition that generates $CO_2$ can be provided to a tree via aperture 37. Aperture 37 enters the tree in a roughly horizontal direction, towards the dead woody interior of the tree. Interior channels 38 are formed in a roughly vertical direction, up a portion of the length of the tree. In some embodiments, interior channels of e.g., 1-2 mm wide may resemble, in shape, the inner sheath of coaxial cable (e.g., having a cylinder-like geometry).

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "plant" refers to any green plant having chloroplasts for photosynthetic reactions. In some embodiments, the plant is a tree. In some embodiments, the plant yields a fruit, vegetable, or nut. In some embodiments, the plant is a vine, or a fruit-bearing vive, such as a grape vine. In some embodiments, the plant is a woody plant. "Woody plant," as used herein, refers to plants having stiff stems with a protective outer coating (bark). Examples of woody plants that can be treated by the methods and apparatus of the invention include, but are not limited to, trees, palms, and shrubs. As used herein, the term "tree" refers to any species of tree, for example, including hardwoods (angiosperms) and softwoods (conifers).

Exemplary non-limiting hardwoods include alder, ash, aspen, balsa, beech, birch, cherry, chestnut, cottonwood, dogwood, elm, eucalyptus, gum, hickory, mahogany, maple, oak, poplar, walnut, and willow. Exemplary non-limiting softwoods include cedar, cypress, fir (e.g., Douglas-fir), yew, hemlock, pine, and spruce.

In the case of woody plants that possess a ringlike cambium layer, e.g., woody dicotyledonous plants (e.g., hardwoods) and woody gymnosperms (e.g., conifers), the composition including $CO_2$ and/or a composition that generates $CO_2$ can be provided into the cambium layer. In some embodiments, the composition including $CO_2$ and/or a composition that generates $CO_2$ can be provided the into the interior of the tree past the cambium layer. In one embodiment, the operator selects points on the trunk (stem) of the plant to be provided. In the case of plants with a thick protective outer later (bark), the points into which injections are to be made may correspond to fissures (cracks) in the bark, in which expansion zone tissue can be seen. "Expansion zone tissue" refers to a layer of tissue beneath the bark, where the plant is actively expanding in girth. Such expansion produces the fissures in the bark. In smooth-barked trees (e.g., beech), injections can be made into lenticels (pores), or through the bark at any point. In the case of woody plants that do not possess a ringlike cambium layer around the stem, e.g., monocotyledonous plants, e.g., palm trees, the composition including $CO_2$ and/or a composition that generates $CO_2$ is provided into the interior of the stem at any depth.

As used herein, the term "transpiration" refers to a process similar to evaporation. It is a part of the water cycle, and it is the loss of water vapor from parts of plants (similar to sweating), especially in leaves but also in stems, flowers and roots. Leaf surfaces are dotted with openings which are collectively called stomata, and in most plants they are more numerous on the undersides of the foliage. The stomata are bordered by guard cells that open and close the pore. Leaf transpiration occurs through stomata, and can be thought of as a necessary "cost" associated with the opening of the stomata to allow the diffusion of carbon dioxide gas from the air for photosynthesis.

Plants regulate, in part, the rate of transpiration by the degree of stomatal opening. The rate of transpiration is also influenced by the evaporative demand of the atmosphere surrounding the leaf such as humidity, temperature, wind and incident sunlight. Soil water supply and soil temperature can influence stomatal opening, and thus transpiration rate. The amount of water lost by a plant also depends on its size and the amount of water absorbed at the roots. Stomatic transpiration accounts for most of the water loss by a plant, but some direct evaporation also takes place through the cuticle of the leaves and young stems. Transpiration also cools plants, changes cell's osmotic pressure, and enables mass flow of mineral nutrients and water from roots to shoots. Increases in the following factors may also increase the rate of transpiration: the number of leaves, the number of stomata, light supply, temperature, and water supply. Decreases in the relative humidity will increase the rate of transpiration.

Transpiration rates of plants can be measured according to methods known to those of skill in the art, including the methods described in U.S. Patent Publication No. 20110270531; "Measurement of Transpiration and Leaf Conductance" Pearcy R W, Schulze E D and Zimmermann R in *Plant Physiological Ecology: Field Methods and Instrumentation* 1989, Eds. R W Pearcy, J Ehleringer, H A Mooney, and P W Rundel, Ch 8, pp 137-160, Chapman and Hall, London; and Groom P, *Elementary Botany,* 1900, G Bell & Sons, London, page 211-214. The transpiration rates of plants can be measured with instruments such as potometers, lysimetes, porometers, photosynthesis systems and heat balance sap flow gauges. In some embodiments, measurements of transpiration loss can be used to control the amount of a composition including $CO_2$ and/or a composition that generates $CO_2$ to be provided to a plant. The amount of water transpired by the plant is re-measured and compared to an initial measurement of water transpiration. If the re-measurement establishes that the amount of water that is transpired by the plant has decreased, the provided concentration of the composition including $CO_2$ and/or a composition that generates $CO_2$ is maintained. If the re-measurement establishes that the amount of water that is transpired by the plant has increased or not decreased, the concentration of the composition including $CO_2$ and/or a composition that generates $CO_2$ may be increased. In an embodiment, measurements on water transpiration from a first plant can be used in order to control the amount of a composition including $CO_2$ and/or a composition that generates $CO_2$ which is provided to a second similar plant. For instance, correlations between water transpiration and $CO_2$-related compositions can be determined from a set of monitored plants, and these correlations can be then used to determine the amount of $CO_2$-related compositions provided to other plants of the same species.

Mass flow of liquid water from the roots to the leaves, i.e., xylem flow, is driven in part by capillary action initiated by transpiration. In taller plants and trees however, the force of gravity can only be overcome by the decrease in hydrostatic (water) pressure in the upper parts of the plants due to the diffusion of water out of stomata into the atmosphere. Water is absorbed at the roots by osmosis, and any dissolved mineral nutrients travel with it through the xylem.

As used herein, the term "stoma" (also stomate; plural stomata) refers to a pore, found in the leaf and stem epidermis that is used for gas exchange. The pore is bordered by a pair of specialized parenchyma cells known as guard cells that are responsible for regulating the size of the opening. The term "stoma" is also used collectively to refer to an entire stomatal complex, both the pore itself and its accompanying guard cells. Air containing carbon dioxide and oxygen enters the plant through these openings where it is absorbed, transported and then used in photosynthesis and respiration, respectively. Oxygen produced by photosynthesis in the spongy layer cells (parenchyma cells with pectin) of the leaf interior exits through these same openings. Also, water vapor is per force released into the atmosphere through these pores via transpiration.

As used herein, the term "translocation" or phloem flow, refers to the transport of soluble organic material made during photosynthesis to all parts of the plant. The soluble organic material may comprise one or more carbohydrates from the leaves. In vascular plants, phloem is the living tissue that carries organic nutrients (known as photosynthate), in particular, carbohydrates such as glucose, to all parts of the plant where needed. In trees, for example, the phloem is the innermost layer of the bark.

As used herein, the term "carbon-based photosynthate" refers to sugars, lipids, proteins, and primary or secondary metabolites that are photosynthesized by the plant. "Sugars" and "one or more carbohydrates from a plant" refer to any sugar, such as glucose or a biosynthetic precursor thereof, that is produced by the plant during photosynthesis or that or a polysaccharide derivative that is produced upon one or more subsequent biotransformations of glucose. In the light-independent or dark reactions of photosynthesis the enzyme RuBisCO captures $CO_2$ and in a process that requires the newly formed NADPH, called the Calvin-Benson Cycle, releases three-carbon sugars, which are later combined to form glucose and more complex carbohydrates. The overall equation for the light-independent reactions in green plants is: $3CO_2 + 9ATP + 6NADPH + 6H^+ \rightarrow C_3H_6O_3\text{-phosphate} + 9ADP + 8P_i + 6NADP^+ + 3H_2O$, where ATP is adenosine-5'-triphosphate, ADP is adenosine diphosphate, $P_i$ is inorganic phosphate, NADPH and $NADP^+$ are the reduced and oxidized forms of nicotinamide adenine dinucleotide phosphate.

The fixation or reduction of carbon dioxide is a process in which carbon dioxide combines with a five-carbon sugar, ribulose 1,5-bisphosphate (RuBP), to yield two molecules of a three-carbon compound, glycerate 3-phosphate (GP), also known as 3-phosphoglycerate (PGA). GP, in the presence of ATP and NADPH from the light-dependent stages, is reduced to glyceraldehyde 3-phosphate (G3P). This product is also referred to as 3-phosphoglyceraldehyde (PGAL) or even as triose phosphate. Triose is a 3-carbon sugar. Most (5 of 6 molecules) of the G3P produced is used to regenerate RuBP so the process can continue. The remaining 1 of 6 molecules of the triose phosphates is not "recycled" and often condenses to form hexose phosphates, which ultimately yield glucose and more complex carbohydrates, such as cellulose. The carbohydrates produced during carbon metabolism yield carbon skeletons that can be used in other metabolic processes like the production of amino acids and lipids.

The quantity of the carbon-based photosynthate that is produced by a plant, according to the methods described herein, during a period of time can and will vary. In some embodiments, the compositions described herein are provided to the plant to increase the quantity of the carbon-based photosynthate that is produced by a plant during a period of time. In this regard, the quantity of the carbon-based photosynthate that is produced by a plant will increase from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about twenty years, or a range between and including any two of these values. In some embodiments, carbon-based photosynthate includes carbon derived from the composition including $CO_2$ and/or a composition that generates $CO_2$. In some embodiments, the plant is grown on a farm, orchard, or in a forest. In some embodiments, the plant is a tree.

In some embodiments, the quantity of carbon-based photosynthate that is produced by a plant, according to the methods described herein, is monitored by taking a first measurement of the quantity of the photosynthate that is produced by a plant during a period of time before providing any of the compositions described herein; and taking a second measurement of the quantity of the photosynthate that is produced by a plant during the period of time after providing any of the compositions described herein, where the second measurement is increased relative to the first measurement. In this regard, the second measurement may increase relative to the first measurement by about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values. In some embodiments, the period of time is at least one week and the second measurement is reduced by at least 25% relative to the first measurement. In some embodiments, the period of time is at least one month and the second measurement is reduced by at least 25% relative to the first measurement. In some embodiments, the plant is grown on a farm, orchard, or in a forest. In some embodiments, the plant is a tree. The amount of photosynthate produced, or its change from a baseline amount, can be correlated with the amount of $CO_2$-related composition provided to the plant. In some embodiments, correlations established from one plant or set of plants can be used to predict behavior in other similar plants.

Compositions

Each embodiment of the compositions described herein can be used with any method, article or apparatus described herein. As used herein, the terms "a composition comprising $CO_2$" and "a composition including $CO_2$" refer to a composition including $CO_2$ gas, dissolved $CO_2$, or a dissolved mixture of $CO_2$, $H_2CO_3$ (carbonic acid), $HCO_3^-$ (bicarbonate), $CO_3^{2-}$ (carbonate), or a combination thereof. In some embodiments, the composition including $CO_2$ is a fluid, gel, or suspension. In some embodiments, the composition including $CO_2$ is an aqueous fluid, an aqueous gel, or an aqueous suspension. Carbon dioxide is soluble, for example, in water in which it reversibly converts to $H_2CO_3$. The relative concentrations of $CO_2$, $H_2CO_3$, and the deprotonated forms $HCO_3^-$ and $CO_3^{2-}$ depend on the pH. In neutral or slightly alkaline water (pH>6.5), the $HCO_3^-$ form predominates (>50%). In very alkaline water (pH>10.4), the predominant (>50%) form is $CO_3^{2-}$.

In some embodiments, the composition comprising at least about 0.1 wt./wt. % $CO_2$ is in a condensed phase (e.g., under >1 atmosphere of pressure or dissolved in a fluid). In some embodiments, the composition that comprises at least about 0.1 wt./wt. % $CO_2$ is a fluid comprising $CO_2$. In some embodiments, the composition that comprises at least about 0.1 vol./vol. % $CO_2$ is a gas comprising $CO_2$.

In some embodiments, the composition including $CO_2$, as described in any of the embodiments herein, includes about 0.1-1.0 (wt./wt. or vol./vol.) % $CO_2$, about 1.0-10.0 (wt./wt. or vol./vol.) % $CO_2$, about 10.0-25.0 (wt./wt. or vol./vol.) % $CO_2$, about 25.0-50.0 (wt./wt. or vol./vol.) % $CO_2$, about 50.0-75.0 (wt./wt. or vol./vol.) % $CO_2$, about 75.0-100.0 (wt./wt. or vol./vol.) % $CO_2$, or a range between and including any two of these values.

As used herein, the term "a composition that generates $CO_2$" refers, in some embodiments, to a composition including a "$CO_2$-precursor compound," or salt thereof, other than $H_2CO_3$ (carbonic acid), $HCO_3^-$ (bicarbonate) or $CO_3^{2-}$ (carbonate), where the $CO_2$-precursor compound can generate $CO_2$. In some embodiments, the $CO_2$-precursor compound, or salt thereof, that generates $CO_2$ is selected from citric acid, cis-aconitic acid, isocitric acid, oxalosuccinic acid, α-ketoglutaric acid, succinic acid, fumaric acid, malic acid, oxaloacetic acid, and combinations thereof. In some embodiments, the composition that generates $CO_2$ further includes an enzyme that catalyzes a conversion or decarboxylation of the $CO_2$-precursor compound. (See, for example, Scheme 1, below.) In some embodiments, the enzyme is selected from NAD-malic enzyme, citrate synthase, aconitase, isocitrate dehydrogenase, α-ketoglutarate dehydrogenase, succinyl coenzyme A synthetase, succinate dehydrogenase, fumarase, malate dehydrogenase, and combinations thereof. In some embodiments, the enzyme includes malate dehydrogenase, NAD-malic enzyme, or a combination thereof. Malate dehydrogenase catalyzes the reduction of oxaloacetic acid to malic acid. NAD-malic enzyme catalyzes the formation of $CO_2$ upon the conversion of malic acid to lactic acid. In some embodiments, the composition that generates $CO_2$ further includes a microorganism including an enzyme that catalyzes a conversion or decarboxylation of the $CO_2$-precursor compound. In some embodiments the microorganism is selected from lactic acid bacteria (LAB), or a functional equivalent of LAB.

Scheme 1

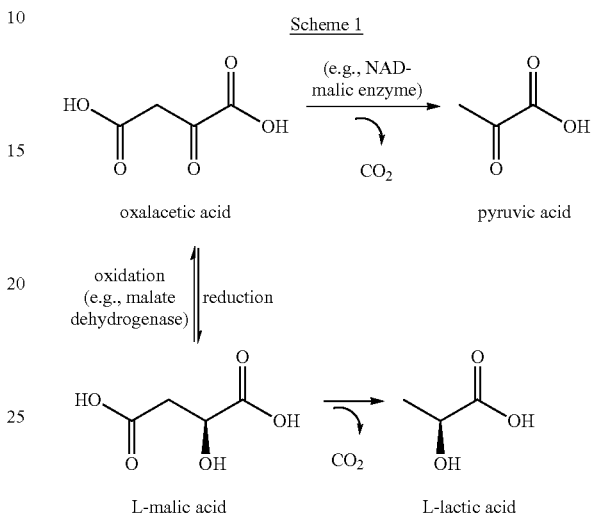

Lactic acid bacteria comprise a Glade of Gram-positive, low-GC, acid-tolerant, generally non-sporulating, non-respiring rod or cocci that are associated by their common metabolic and physiological characteristics. These bacteria, usually found in decomposing plants and lactic products, produce lactic acid as the major metabolic end-product of carbohydrate fermentation. Genera included among LAB include *Lactobacillus, Leuconostoc, Pediococcus, Lactococcus*, and *Streptococcus* as well as the more peripheral *Aerococcus, Carnobacterium, Enterococcus, Oenococcus, Sporolactobacillus, Tetragenococcus, Vagococcus*, and *Weisella*, which belong to the order Lactobacillales.

In some embodiments, the plant (e.g., tree) includes an enzyme that catalyzes the generation of $CO_2$ from the $CO_2$-precursor compound. In some embodiments, the plant (e.g., tree) includes a microorganism, such as a LAB, that includes an enzyme that catalyzes conversion or decarboxylation of the $CO_2$-precursor compound. In some embodiments, a composition, as described herein, is added to the plant that increases the concentration of a microorganism and/or enzyme that catalyzes conversion or decarboxylation of the $CO_2$-precursor compound.

As used herein, the term "a composition that generates $CO_2$" additionally refers, in some embodiments, to a composition that is prepared by the reaction of an amine, or a salt thereof, with $CO_2$. After the reaction product of an amine and $CO_2$ is formed, the $CO_2$-enriched reaction product is provided into a plant, such as a tree, where it sheds $CO_2$ and regenerates the starting amine. Non-limiting examples of an amine include ammonia, a primary amine, a secondary amine, a tertiary amine, or a salt thereof. Representative amines include primary ($C_6$-$C_{30}$) alkyl amines, cyclic amines such as piperidine or morpholine, monoethanolamine (MEA), diethanolamine (DEA), methyldiethanolamine (MDEA), diisopropylamine (DIPA), aminoethoxyethanol (diglycolamine) (DGA), or a combination thereof.

In some embodiments, the composition that generates $CO_2$ is prepared by the reaction of an amine, or a salt thereof, with $CO_2$. After the reaction product of an amine and $CO_2$ is formed, the reaction product is provided into a plant, such as a tree, where it sheds $CO_2$ and regenerates the starting amine. Non-limiting examples of an amine include ammonia, a primary amine, a secondary amine, a tertiary amine, or a salt thereof. For example, the composition that generates $CO_2$ may include an aqueous solution of one or more amines such as those commonly used to "scrub" $CO_2$ from a solution, or from a mixture of gasses, in the oil industry. Representative amines used for $CO_2$ scrubbing include primary ($C_6$-$C_{30}$) alkyl amines, cyclic amines such as piperidine or morpholine, monoethanolamine (MEA), diethanolamine (DEA), methyldiethanolamine (MDEA), diisopropylamine (DIPA), aminoethoxyethanol (diglycolamine) (DGA), or a combination thereof. See for example the amines disclosed in G. T. Rochelle et al., "Amine Scrubbing for $CO_2$ Capture," *Science*, Sep. 25, 2009: 1652-1654, in the references cited therein, and in the published presentation by H. Dang and G. T. Rochelle, "$CO_2$ Absorption Rate and Solubility in Monoethanolamine/piperazine/Water," given at the *First National Conference on Carbon Sequestration*, Washington, D.C., May 14-17, 2001, and in the references cited therein. Some typical amine concentrations, expressed as weight percent of pure amine in the aqueous solution, can be 5%, 10%, 20%, 30%, 40%, 50%, 75%, 100%, or a concentration between any two of these values.

A representative reaction product of an amine, or a salt thereof, with $CO_2$ can be prepared by contacting an aqueous amine solution with $CO_2$ that is either supplied in relatively pure form or obtained from the surrounding atmosphere. The amine solution "scrubs" or captures the $CO_2$ and thus forms a composition that generates $CO_2$ (i.e., substantially enriched with $CO_2$) which may then be provided into a plant, such as a tree. Once provided, the composition that generates $CO_2$ will shed $CO_2$, thereby delivering $CO_2$ to the tree and regenerating the amine solution (i.e., substantially lacking $CO_2$), which can be recovered from the tree. After recovery, the amine solution can be recycled by recontacting the amine solution with additional $CO_2$ to recapture $CO_2$ and regenerate the composition that generates $CO_2$ for additional administration into the tree.

The preparation and use of an amine-based composition that generates $CO_2$ may further include an absorber unit and/or a regenerator unit as well as any related accessory equipment. Absorber units, such as those routinely used in the oil industry, increase the rate and/or efficiency by which the amine solution absorbs $CO_2$, that is supplied in relatively pure form or obtained from the surrounding atmosphere, to produce an amine solution rich in the absorbed $CO_2$. For example, the absorber unit may attain temperatures of, for example, 20° C.-200° C., and/or pressures of, for example, 1-10,000 atmospheres. The resulting amine solution, now rich in the absorbed $CO_2$, is then routed into the tree, $CO_2$ is shed from solution into the tree, and the amine solution, now substantially lacking $CO_2$, is recovered from the tree and optionally regenerated with additional $CO_2$. Optionally, a regenerator unit is located on or inside the tree to increase the rate at which $CO_2$ is shed from the amine solution to produce free $CO_2$ that is provided into the tree. As such, the absorber unit is generally located outside the tree, whereas the regenerator unit can be located inside or outside the tree. In some embodiments, one or more absorber units and/or regenerator units are operatively connected to one or more of components (a)-(i) of the apparatus, described herein, for coordinating the input of a composition including at least about 0.1 (wt./wt. or vol./vol.) % $CO_2$ and/or a composition that generates $CO_2$ into plants and the extraction of the carbon-based photosynthate from plants. In some embodiments, the absorber units and/or regenerator units are miniature versions of those known to one of ordinary skill in the art of $CO_2$ capture. See for example the absorber units and/or regenerator units disclosed in Rochelle et al., "Amine Scrubbing for $CO_2$ Capture," *Science*, Sep. 25, 2009: 1652-1654, and in the references cited therein.

In some embodiments, any of the compositions that generates $CO_2$ may form micelles that carry "payloads" of $CO_2$ and assist in the delivery of $CO_2$ to the tree. For example, the composition that generates $CO_2$ may form micelles that include surfactants in addition to either an $CO_2$-precursor compound, as described above, or one or more amines such as a primary ($C_6$-$C_{30}$) alkyl amine, cyclic amines such as piperidine or morpholine, monoethanolamine (MEA), diethanolamine (DEA), methyldiethanolamine (MDEA), diisopropylamine (DIPA), aminoethoxyethanol (diglycolamine) (DGA), or a combination thereof. These micelles may further carry "payloads" that include a nutrient, microbicide, fungicide, antibacterial agent, antiviral agent, insecticide, plant hormone agent, plant growth modulator, anti-herbivore agent, fertilizer, or a mixture thereof. Thus, the micelles may likewise assist in the delivery of any of these agents into the tree.

In some embodiments, any of the compositions that generates $CO_2$ may include about 0.1-1.0 wt./wt. % of the $CO_2$-precursor compound, about 1.0-10.0 wt./wt. % of the $CO_2$-precursor compound, about 10.0-25.0 wt./wt. % of the $CO_2$-precursor compound, about 25.0-50.0 wt./wt. % of the $CO_2$-precursor compound, about 50.0-75.0 wt./wt. % of the $CO_2$-precursor compound, about 75.0-100.0 wt./wt. % of the $CO_2$-precursor compound, or a range between and including any two of these values.

In some embodiments, the composition comprising $CO_2$ and/or the composition that generates $CO_2$ further includes water. In some embodiments, the composition comprising $CO_2$ and/or the composition that generates $CO_2$ further includes an excipient. In some embodiments, the composition comprising $CO_2$ and/or the composition that generates $CO_2$ further includes an excipient selected from a fungicide, antibiotic, antiviral, pesticide, growth regulator, nutrient, anti-herbivore agent, fertilizer, stomata control agent and a combination thereof. In some embodiments, the composition including at least about 0.1 (wt./wt. or vol./vol.) % $CO_2$ and/or a composition that generates $CO_2$ further includes from about 0.01 wt./wt. % to about 1 wt./wt. %, from about 1 wt./wt. % to about 5 wt./wt. %, from about 5 wt./wt. % to about 15 wt./wt. %, from about 15 wt./wt. % to about 25 wt./wt. %, from about 25 wt./wt. % to about 50 wt./wt. %, or a range between and including any two of these values, of one or more excipients as described herein.

In some embodiments, the composition that generates $CO_2$ is a fluid, gel, aerosol, solution, or a suspension or a component thereof. In some embodiments, the composition including $CO_2$ and/or a composition that generates $CO_2$ is a fluid. In some embodiments the composition including $CO_2$ and/or a composition that generates $CO_2$ is a gel. In some embodiments the composition including $CO_2$ and/or a composition that generates $CO_2$ is a suspension. In some embodiments the composition including $CO_2$ and/or a composition that generates $CO_2$ is an aerosol. In some embodiments the composition including $CO_2$ and/or a composition that generates $CO_2$ is a solution.

In some embodiments, the compositions described herein, including $CO_2$ and/or generating $CO_2$, further include an excipient. In some embodiments, the excipient is selected from a fungicide, antibiotic, antiviral, pesticide, growth regulator, nutrient, anti-herbivore agent, fertilizer, stomata control agent and a combination thereof. The composition may be a fluid (e.g., solution), gel, an aerosol, or a suspension including such excipients.

Exemplary non-limiting fungicides include, but are not limited to, copper chelate, which is used to treat ash yellows, Dutch elm disease and fruit tree-related fungus problems; mefenoxam ((R)-2[(2,6-dimethylphenyl)-metho-xyacetylamino]-propionic acid methyl ester), which is used to treat certain diseases in conifers, nonbearing citrus, nonbearing deciduous fruits and nuts, ornamentals and shade trees; propiconazole, which is used to treat broad spectrum systemic disease control for evergreens, ornamentals and shade trees; and others. For instance, 14.3% propaconazole can be applied at a rate of 10 ml per 2.54 cm (1 inch) diameter of e.g., to control Dutch elm disease in elm, and oak wilt in oak.

Exemplary non-limiting antibiotics include, but are not limited to oxytetracycline and streptomycin.

Exemplary non-limiting pesticides include, but are not limited to, Decathlon® (cyfluthrin; OHP, Inc., Mainland, Pa.) which is used to control pests such as ants, crickets, spiders, etc.; abamectin B1, which is used for insect pest control for woody trees and shrubs for beetles, lace bugs, spider mites and leaf miners; imidacloprid, which is used for broad spectrum control for adelgid, armored scales, Asian longhorned beetle, aphids, elm leaf beetles, black vine weevil larvae, eucalyptus longhorned borer, flatheaded borers (including bronze birch borer and alder-birch borer), Japanese beetles, lace bugs, leaf hoppers, leaf miners, mealy bugs, sawfly larvae, pine tip moth larvae, psyllids, royal palm bugs, scale insects, thrips, and whiteflies; azadirachtin, which is used for insect pest control for aphids, armyworms, bagworms, beetles, grubs and weevils, cankerworms, caterpillars, loopers and moths, chafers, cutworms, flies, greenhouse leaf tiers, leaf hoppers, leaf miners, leaf rollers, leaf perforators, marsh crane flies, mealy bugs, psyllids, sawflies, thrips and whiteflies; nicotine sulfate, which is used for control of mites. For instance, 10% imidacloprid can be applied at a rate of 2 ml per 2.54 cm (1 inch) diameter to trees for control of wooly adelgid.

Exemplary non-limiting growth regulators include, but are not limited to, potassium salts of 6-hydroxy-3-(2H)-pyridazinone, which is used as a growth inhibitor and retardants for shade trees, evergreens and ornamentals, and ethylene, which is a plant auxin used to inhibit seed set in invasive trees.

Exemplary non-limiting nutrients and fertilizers include, but are not limited to, 18-3-4 spring/fall fertilizer (e.g., "Dean's Green," Blackstone Ag Inc., Mesa, Ariz., USA); 5-10-5 summer/winter fertilizer (e.g., "Nutra-green," Blackstone Ag Inc., Mesa, Ariz., USA), fulvic acid (e.g., "LM-32," Blackstone Ag Inc., Mesa, Ariz., USA), 14-2-3 fertilizer (e.g., "Enhance," Blackstone Ag Inc., Mesa, Ariz., USA), ammonia, orthophosphate, chelates, calcium nitrate, calcium, magnesium, phosphorus, potassium, sulfur, boron, cobalt, copper, iron, manganese, molybdenum, zinc, etc., and combinations thereof.

In some embodiments, the compositions described herein, including $CO_2$ and/or generating $CO_2$, further include a stomata control agent. Exemplary non-limiting embodiments of stomata control agent comprise abscisic acid or a salt or precursor thereof. The composition may be a fluid (e.g., solution), gel, an aerosol, or a suspension.

Providing Compositions into Plants

Each of the compositions described herein can be provided into a plant, via any article or apparatus described herein, according to any of the methods described herein for providing a composition into a plant. In some embodiments, a composition including $CO_2$ and/or a composition that generates $CO_2$ is provided into the plant with an injection needle. The needle can be of any length sufficient to access the vascular system of the plant, such as a tree. For example, the needle can be from about 0.1 cm (0.04 inches) to about 10.0 cm (4.0 inches) long, or any intermediate length, with at least one small aperture at the distal end of the needle. The purpose of this needle is to inject the composition including $CO_2$ and/or a composition that generates $CO_2$ into a tree such as a hardwood or softwood tree. The needle can be made of steel, stainless steel, aluminum, glass, plastic, or other similar materials.

In some embodiments, a composition including $CO_2$ and/or a composition that generates $CO_2$, is provided into one or more interior channels that have been created within the plant. Such channels can generally be created by boring into the plant to create one or more openings into which the $CO_2$ or the composition that generates $CO_2$ can be deposited, and from which the $CO_2$ or the composition that generates $CO_2$ will gradually leach into the plant. Such channels or openings can be created by using any wood-boring tool known to one of ordinary skill. For example, a channel-boring device can be used that resembles the shape of an endoscope, but has a cutting mechanism at its tip. The endoscopic-type cutting device can bore an aperture, in a roughly horizontal direction, towards the dead woody interior of a tree. The endoscopic-type cutting device can then turn upward and bore interior channels, in a roughly vertical direction, up a portion of the length of the tree. Further, the device can be used to widen the vertical channels within the interior of the tree. In some embodiments, a resulting channel of e.g., 1-2 mm wide is expanded within the interior of the tree until the hollowed channel resembles, in shape, the inner sheath of coaxial cable (e.g., having a cylinder-like geometry).

In some embodiments, a composition including $CO_2$ and/or a composition that generates $CO_2$ is provided into one or more of such interior channels within the tree. Thus provided, the composition including $CO_2$ and/or a composition that generates $CO_2$, is allowed to diffuse or soak from the relatively dead and woody interior channels into the xylem of the tree. In some embodiments, the interior channels are located close to the xylem. In some embodiments, the composition including $CO_2$ and/or a composition that generates $CO_2$ will be provided into xylem and the carbon-based photosynthate will be extracted from the phloem.

Alternatively or additionally, the composition including $CO_2$ and/or a composition that generates $CO_2$ can be allowed to diffuse or soak from the interior channels into the phloem of the tree. In some embodiments, the interior channels are located close to the phloem. In some embodiments, the composition including $CO_2$ and/or a composition that generates $CO_2$ will be provided into the phloem and the carbon-based photosynthate will be extracted from the xylem.

Alternatively or additionally, the composition including $CO_2$ and/or a composition that generates $CO_2$ can be allowed to diffuse or soak into the plant from its leaves or roots. In some embodiments, the composition is applied to the leaves of a plant by a spray or as a coating. In some embodiments, the composition will be provided to the roots of the plant as a fluid (by itself or within a solution).

In some embodiments, the composition including $CO_2$ and/or a composition that generates $CO_2$, of any of the embodiments described herein, is provided into or proximate to the vasculature system of the plant. In some embodiments the composition including $CO_2$ and/or a composition that generates $CO_2$ is provided into or near cells of the plant that are substantially dead. In some embodiments the composition including $CO_2$ and/or a composition that generates $CO_2$ is provided into or near the xylem of the plant. In some embodiments the composition including $CO_2$ and/or a composition that generates $CO_2$ is provided into or near cells of the plant that are substantially alive. In some embodiments the composition including $CO_2$ and/or a composition that generates $CO_2$ is provided into or near the phloem of the plant. In some embodiments, the plant is grown on a farm, orchard, or in a forest. In some embodiments, the plant is a tree.

In some embodiments, the tree is grown on a farm, orchard, or in a forest. In some embodiments, the tree is a hardwood selected from alder, ash, aspen, balsa, beech, birch, cherry, chestnut, cottonwood, dogwood, elm, eucalyptus, gum, hickory, mahogany, maple, oak, poplar, walnut, and willow. In some embodiments, the tree is a softwood selected from softwoods include cedar, cypress, fir (e.g., Douglas-fir), yew, hemlock, pine, and spruce.

In some embodiments, some of the cells of the native vascular system of the tree have been removed and replaced with a substitute vascular system. For example, some or all of the native xylem of the plant have been removed and replaced, at least in part, with substitute xylem. The substitute xylem may be made of any material, such a wood, plastic, resin, or a combination thereof. In some embodiments, the substitute xylem includes a material having pores through which the composition including $CO_2$ and/or a composition that generates $CO_2$ is circulated through the tree.

In some embodiments, the carbon-based photosynthate is extracted from or near the phloem of the plant. Additionally, some or all of the native phloem of the plant have been removed and replaced with substitute phloem. The substitute phloem may comprise any material, such a wood, plastic, resin, metal or a combination thereof. In some embodiments, the substitute phloem includes a material having pores through which the carbon-based photosynthate is extracted from the phloem of the plant. In some embodiments, the carbon-based photosynthate includes sap. In some embodiments, the carbon-based photosynthate includes glucose, stachyose, or sugar alcohols such as sorbitol. In some embodiments, the plant is grown on a farm, orchard, or in a forest. In some embodiments, the plant is a tree.

In some embodiments, compositions described herein can be provided to a plant to increase the plant's rate of translocation during a period of time. The translocation rates of plants can be measured according to methods known to those of skill in the art. In this regard, the rate of translocation may increase from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values. In some embodiments, the plant is grown on a farm, orchard, or in a forest. In some embodiments, the plant is a tree.

In some embodiments, compositions described herein can be provided to a plant to decrease the plant's rate of absorption of atmospheric $CO_2$ over the period of time. In this regard, the rate of absorption of atmospheric $CO_2$ by the plant may be reduced from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values.

The rate of absorption of atmospheric $CO_2$ by a plant can be measured according to methods known to those of skill in the art, including the methods described in U.S. Patent Publication No. 20100043096. The $CO_2$ absorption rates of plants can be measured with instruments such as a Li-6400 photosynthesis system (Li-Cor, Inc., Lincoln, Nebr., USA).

"Smart" Sensors and Pumps

According to another aspect, an apparatus is provided for coordinating the input of a composition including $CO_2$ and/or a composition that generates $CO_2$ into the plant(s) and the extraction of the carbon-based photosynthate from the plant(s). The apparatus can include one or more of each of the following components: (a) an infusion pump for delivering the composition including $CO_2$ and/or the composition that generates $CO_2$ into the tree, (b) an extraction pump for extracting the carbon-based photosynthate from the tree, (c) a receptacle containing the composition including $CO_2$ and/or the composition that generates $CO_2$ and/or a receptacle containing carbon-based photosynthate, (d) a sensor, (e) a control unit (i.e., "process controller") including a microprocessor, electrically connected to the infusion pump and the sensor, (f) a user interface, optionally including a display, operatively connected to the control unit, (g) an absorber unit, operatively connected to the control unit, (h) a regenerator unit, operatively connected to the control unit, and (i) a communications interface operatively connected to one or more of components (a)-(h) and optionally adapted for wireless communication. Each of components (a)-(i) may be combined into an integrated apparatus. Alternatively, one or more of components (a)-(i) may be used remotely from the other components. Components (a)-(i) may interface via wiring, (e.g., via hard wiring, a serial port, a USB port, a "fire wire" port, etc.), or in a wireless fashion (e.g., connected an via infrared connection, a radio frequency connection, a "bluetooth" connection, etc.).

The Infusion and Extraction Pumps (a)-(b):

Suitable pumps are well known in the art and in industries such as the oil industry (e.g., for the injection or extraction of subsea fluids) or the healthcare industry (e.g., for the infusion of fluids into a patient). See, e.g., U.S. patent application Ser. No. 09/434,974; and U.S. Pat. Nos. 6,270,478; 6,213,738; 5,743,878; 5,665,070; 5,522,798; and 5,171,301, each of which is hereby incorporated by reference in its entirety. Such pumps can be simple pumps which are either "on" or "off," or may comprise a programmable controller (referred to in the art as a "smart pump") that may be integral to the pump or exist as a separate controller unit interfaced in a wired (e.g., via hard wiring, a serial port, a USB port, a "fire wire" port, etc.) or wireless fashion (e.g., connected an via infrared connection, a radio frequency connection, a "bluetooth" connection, etc.). Each of the pumps may communicate with components (a)-(i). In one embodiment each of the pumps may include technology (e.g., bluetooth) for wireless communication. Where additional information is available from components (a)-(i) it is contemplated that the control unit of the pumps may be programmed or otherwise configured to collect the information and use the information to modify infusion and/or extraction rates.

The Receptacles (c):

Each receptacle of the apparatus is used to store a supply, for example, of either the composition including $CO_2$ and the composition that generates $CO_2$ or the carbon-based photosynthate. Additional receptacles can optionally be used to store one or more excipients that modulate plant growth (e.g., antivirals or any agent to accelerate or retard root growth). Alternatively, such excipients can be combined in a single receptacle with the composition including $CO_2$ and/or the composition that generates $CO_2$. The receptacle can be of any size or shape and consist of any material such as plastic, metal, or glass.

The Sensors (d):

One or more sensors are used to obtain and monitor data related to the plant. Each sensor is independently located in the vicinity of the plant, within the plant, or on the surface of the plant. Each sensor can be used to obtain and monitor data, for example, related to the concentration of $H_2O$, $CO_2$, composition that generates $CO_2$, or carbon-based photosynthate. Each sensor can also be used to obtain and monitor data, for example, related to atmospheric temperature, plant temperature, humidity, plant moisture level, wind speed, sunlight level, the amount of water provided to the plant, the transpiration rate of the plant, guard cell morphology (e.g., expansion or contraction), the rate of injection of $CO_2$ or composition that generates $CO_2$ into the plant, or the rate of extraction of carbon-based photosynthate from the plant. The sensors obtain and monitor such data related to the plant and provide the data to the control unit including a microprocessor.

The Control Unit and User Interface (e)-(f):

The control unit including a microprocessor receives data related to the plant from the sensors, as described above, to coordinate and optimize the administration of the composition including $CO_2$ and/or the composition that generates $CO_2$ into the plant, or the rate of extraction of carbon-based photosynthate from the plant. For example, the control unit can set initial irrigation rates, rates at which the composition including $CO_2$ and/or the composition that generates $CO_2$ is provided to the plant, and rates at which carbon-based photosynthate is extracted from the plant. After receiving data from the sensors, the control unit can adjust and optimize such initial rates. For example, the control unit can adjust initial rates, of the administration of the composition including $CO_2$ and/or the composition that generates $CO_2$ into the plant, to levels that enable the plant to reduce transpiration and thus minimize water consumption. The control unit can coordinate the components (a)-(d), (f) and (g) necessary to monitor a single plant. Alternatively, the control unit can coordinate numerous components (a)-(d), (f) and (g) that are necessary to monitor many plants throughout a geographical area. Also, one or more user interfaces, such as those commonly used in the art, can be included anywhere within the apparatus. Each user interface optionally includes a display, such as a touch screen display, and various manual inputs.

The Absorber Units and/or Regenerator Units (g)-(h):

Absorber units, such as those routinely used in the oil industry, increase the rate and/or efficiency by which the amine solution absorbs $CO_2$, that is supplied in relatively pure form or obtained from the surrounding atmosphere, to produce an amine solution rich in the absorbed $CO_2$. Optionally, a regenerator unit is located on or inside the tree to increase the rate at which $CO_2$ is shed from the amine solution to produce free $CO_2$ that is provided into the tree. As such, the absorber unit is generally located outside the tree, whereas the regenerator unit can be located inside or outside the tree. In some embodiments, the absorber units and/or regenerator units are miniature versions of those known to one of ordinary skill in the art of $CO_2$ capture. See for example the absorber units and/or regenerator units disclosed in Rochelle et al., "Amine Scrubbing for $CO_2$ Capture," *Science*, Sep. 25, 2009: 1652-1654, and in the references cited therein.

The Communications Interface (i):

The communications interface facilitates the exchange of information between components (a)-(h) and may consist of wiring, (e.g., via hard wiring, a serial port, a USB port, a "fire wire" port, etc.), of physically removable storage media (e.g., an SD card, a flash drive, etc.), or wireless connections (e.g., connected an via infrared connection, a radio frequency connection, a "bluetooth" connection, etc.).

In some embodiments, the above-described apparatus is automated to control the rates at which the composition including $CO_2$ and/or the composition that generates $CO_2$ are provided (e.g., injected) and the rate of extraction of carbon-based photosynthate. In some embodiments, the rate of injection or the rate of extraction is substantially constant over the period of time. In some embodiments, injection and/or extraction is conducted under pressure. In this regard, the pressure may be in excess of one pound per square inch (psi, 0.007 MPa), such as from about 1 psi to about 100 psi (0.7 MPa), or from about 100 psi to about 1000 psi (7 MPa), or a range between and including any two of these values.

In some embodiments, the rate of injection or the rate of extraction is not substantially constant over the period of time. In this regard, the rate of injection or the rate of extraction may fluctuate depending a condition, where exemplary non-limiting conditions include temperature, the time of day or night, the number of hours of sunlight in a day, humidity, dew point, and average daily rainfall.

Modified Plants

In some embodiments the plant, that is provided the composition including $CO_2$ and/or the composition that generates $CO_2$ and from which carbon-based photosynthate extracted, is a wild-type plant. In some embodiments, the plant has been conventionally bred or genetically engineered. In some embodiments, the plant has been conventionally bred or genetically engineered to consume a reduced amount of water over a period of time relative to a corresponding wild-type plant. In this regard, the quantity of water that is consumed by a conventionally bred or genetically engineered plant may decrease from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values. In some embodiments, the plant is grown on a farm, orchard, or in a forest. In some embodiments, the plant is a tree.

In some embodiments the plant is conventionally bred or genetically modified to reduce their requirement for water. For example, the plants may be conventionally bred or transformed with genes coding for proteins, such as enzyme phosphoenolpyruvate (PEP) carboxylase (PEPC), that facilitate the fixation of carbon according to the crassulacean acid metabolism (CAM) in plants. Such plants that utilize CAM-based photosynthesis generally include plants that are indigenous to arid environments and whose stomata generally shut during the day to minimize water loss and open at night to absorb $CO_2$. Non-limiting examples of such plants include various species of palm trees and pineapple trees, and further include *Clusia aripoensis, Clusia rosea, Clusia minor*, and *Mesembryanthemum crystallinum*. Methods of transforming plants with genes coding for proteins that facilitate the fixation of carbon according to CAM in plants, are known to those of skill in the art. See, for example, Haider M S, et al., J Exp Bot. 2012 March; 63(5):1985-96; Mallona I, et al., Plant Physiol. 2011 August; 156(4): 1978-89; Patel M and Berry J, Exp Bot. 2008; 59(7):1875-94; and Cushman, Plant Physiology, December 2001 vol. 127 no. 4 1439-1448, and the references cited therein.

Additionally, the plants can be conventionally bred or genetically modified to disrupt genes related their stomata. This may be used to produce plants with fewer stomata, with smaller stomata, or to modify the mechanism by which the stomata are opened. As such, the resulting plants that are conventionally bred or genetic disrupted include stomata that are substantially closed or inhibited from opening and thus display reduced levels of water loss from transpiration. Methods of disrupting genes in plants, such as the 1-deoxy-D-xylulose-5-phosphate reductoisomerase (DXR) gene, that are related to the mechanism by the stomata are opened, are known to those of skill in the art. See for example, Xing, et al., *Cell Research* (2010) 20:688-70, and the references cited therein.

In some embodiments, the plant has been conventionally bred or genetically engineered to produce a greater quantity of carbohydrates over a period of time relative to a corresponding wild-type plant. In this regard, the quantity of the carbon-based photosynthate that is produced by a conventionally bred or genetically engineered plant may increase from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values. In some embodiments, the plant has been conventionally bred or genetically engineered to have fewer stomata relative to the wild-type plant. In some embodiments, the plant is grown on a farm, orchard, or in a forest. In some embodiments, the plant is a tree.

In some embodiments, the tree is a hardwood selected from alder, ash, aspen, balsa, beech, birch, cherry, chestnut, cottonwood, dogwood, elm, eucalyptus, gum, hickory, mahogany, maple, oak, poplar, walnut, and willow. In some embodiments, the tree is a softwood selected from softwoods include cedar, cypress, fir (e.g., Douglas-fir), yew, hemlock, pine, and spruce.

Methods and Articles for Reducing Water Consumption and the Rate of Transpiration According to one aspect, a method is provided for reducing the amount of water removed from soil by a plant over an interval of time, comprising providing the plant with a composition that is at least one of a composition comprising at least about 0.1 (wt./wt. or vol./vol.) % $CO_2$ or at least about 0.1 wt./wt. % of a composition that generates $CO_2$.

Without being bound by theory, the water requirements of the plant may be reduced, in part, due to the ability of the composition including $CO_2$ and/or the composition that generates $CO_2$ to modulate stomata activity within the plant. In particular the composition including $CO_2$ and/or the composition that generates $CO_2$ may modulate stomata by preventing or inhibiting the opening of these cells. In some embodiments, the method is conducted in an arid environment, such as a desert.

In some embodiments, the method further includes removing a carbon-based photosynthate from the plant. In some embodiments, the method further includes monitoring the amount of water transpired from a plant. In some embodiments, the method further includes correlating the amount of water transpired by a plant with the amount of composition provided to the plant. In some embodiments, the method further includes monitoring the amount of water removed from soil by a plant. In some embodiments, the method further includes correlating the amount of water removed from soil by a plant with the amount of composition provided to the plant. In some embodiments, the method further includes adjusting the amount of the composition that is provided to the plant or the amount of carbon-based photosynthate that is removed from the plant. In some embodiments, the adjustment is based upon the amount of water removed from soil by a plant. In some embodiments, the adjustment is based upon the amount of water transpired by a plant. In some embodiments, the rate of transpiration by the plant is reduced over the period of time.

In some embodiments, the method further includes extracting a carbon-based photosynthate from the plant in fluid form without any external cutting. In some embodiments, the plant is grown on a farm, orchard, or in a forest. In some embodiments, the plant is a tree. In this regard, the quantity of the carbon-based photosynthate that is produced by a plant may increase from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about fifty years, or a range between and including any two of these values. In some embodiments, the plant is grown on a farm, orchard or in a forest. In some embodiments, the plant is a tree.

In some embodiments of the method, the composition comprising at least about 0.1 wt./wt. % $CO_2$ is in a condensed phase (e.g., under >1 atmosphere of pressure or dissolved in a fluid). In some embodiments, the composition that comprises at least about 0.1 wt./wt. % $CO_2$ is a fluid comprising $CO_2$. In some embodiments, the composition that comprises at least about 0.1 vol./vol. % $CO_2$ is a gas comprising $CO_2$. In some embodiments, the composition comprising at least about 0.1 (wt./wt. or vol.vol.) % $CO_2$ comprises at least about 1.0 (wt./wt. or vol./vol.) % $CO_2$. In some embodiments, the composition comprising at least about 0.1 (wt./wt. or vol.vol.) % $CO_2$ comprises at least about 10.0 (wt./wt. or vol./vol.) % $CO_2$.

In some embodiments of the method, the composition that generates $CO_2$ includes the reaction product of an amine, or a salt thereof, and $CO_2$. In some embodiments, the amine is ammonia, a primary ($C_6$-$C_{30}$) alkyl amine, piperidine, morpholine, monoethanolamine (MEA), diethanolamine (DEA), methyldiethanolamine (MDEA), diisopropylamine (DIPA), aminoethoxyethanol (DGA), or a combination thereof.

In some embodiments of the method, the composition that generates $CO_2$ includes a $CO_2$-precursor compound, or salt thereof, selected from citric acid, cis-aconitic acid, isocitric acid, oxalosuccinic acid, $\alpha$-ketoglutaric acid, succinic acid, fumaric acid, malic acid, oxaloacetic acid, and a combination thereof.

In some embodiments of the method, the composition that generates $CO_2$ further includes an enzyme that catalyzes a conversion or decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or decarboxylation of the $CO_2$-precursor compound. In some embodiments, the microorganism is a lactic acid bacterium.

In some embodiments of the method, the composition that generates $CO_2$ further includes an enzyme that catalyzes a conversion or a decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or a decarboxylation of the $CO_2$-precursor compound. In some embodiments, the microorganism is a lactic acid bacterium.

In some embodiments of the method, the composition further includes water. In some embodiments, the composition further includes an excipient. In some embodiments, the excipient is selected from a fungicide, antibiotic, antiviral, pesticide, growth regulator, nutrient, anti-herbivore agent, fertilizer, stomata control agent and a combination thereof. In some embodiments, the composition further includes a stomata control agent. In some embodiments, the stomata control agent includes abscisic acid or a salt or precursor thereof.

In some embodiments of the method, the composition is included within a fluid, gel, an aerosol, a solution, or a suspension. In some embodiments, the composition is provided into the vasculature system of the plant or to the immediate proximity thereof. In some embodiments, the composition is provided into the phloem or xylem of the plant or to the immediate proximity thereof. In some embodiments, the composition is provided to the plant by injecting the composition into the plant. In some embodiments, the composition is provided to a leaf or root of the plant or to the immediate proximity thereof. In some embodiments, some of the cells of the native vascular system of the tree have been removed and replaced with a functional substitute.

In some embodiments of the method, the carbon-based photosynthate is extracted from the phloem or xylem of the plant or from the immediate proximity thereof. In some embodiments, the carbon-based photosynthate includes a carbohydrate. In some embodiments, the method further includes increasing the quantity of the carbon-based photosynthate that is produced by the plant during an interval of time. In some embodiments, the method further includes monitoring the quantity of the carbon-based photosynthate that is produced by a plant during an interval of time. In other embodiments, the method further includes monitoring the quantity of the carbon-based photosynthate that is produced by a plant during an interval of time. In some embodiments, the method further includes correlating the quantity of the carbon-based photosynthate that is produced by a plant with the amount of composition provided to the plant.

In some embodiments, the method further includes correlating the quantity of the carbon-based photosynthate that is produced by a plant with the amount of composition provided to the plant. In some embodiments, the interval of time is at least one week and the quantity is increased by at least 10%.

In some embodiments, the method further includes increasing the rate of translocation by a plant during an interval of time. In some embodiments, the interval of time is at least one week and the rate of translocation is increased by at least 10%.

In some embodiments, the method further includes decreasing the rate of absorption of atmospheric $CO_2$ by the plant during an interval of time. In some embodiments, the interval of time is at least one week and the rate of absorption of atmospheric $CO_2$ is decreased by at least 10%.

In some embodiments of the method, the carbon-based photosynthate includes carbon derived in part from the composition that is provided to the plant. In some embodiments, the method is at least partially automated. In some embodiments, the composition is provided under positive pressure up to about 1,000 pounds per square inch (7 MPa). In some embodiments, the plant is a wild-type plant or is a domesticated plant. In some embodiments, the plant has been genetically engineered. In some embodiments, the plant has been bred or genetically engineered to consume a reduced amount of soil-derived water over an interval of time relative to a corresponding wild-type plant. In some embodiments, the plant has been bred or genetically engineered to produce a greater quantity of carbon-based photosynthate over an interval of time relative to a corresponding wild-type plant. In some embodiments, the plant has been bred or genetically engineered to have fewer stomata relative to a corresponding wild-type plant. In some embodiments, the plant has been bred or genetically engineered to have smaller stomata relative to a corresponding wild-type plant. In some embodiments, the plant has been bred or genetically engineered to have stomata which are less open relative to a corresponding wild-type plant.

In some embodiments, plant is grown on a farm, orchard, or in a forest. In some embodiments, the plant is a tree. In some embodiments, the tree is a hardwood selected from an alder, ash, aspen, balsa, beech, birch, cherry, chestnut, cottonwood, dogwood, elm, eucalyptus, gum, hickory, mahogany, maple, oak, poplar, walnut, and willow.

In some embodiments, the tree is a softwood selected from a cedar, cypress, fir, yew, hemlock, pine, and spruce.

In some embodiments, the method further includes taking a first measurement of the amount of water removed from soil by a plant over a period of time; providing the plant with a composition that is at least one of a composition comprising at least about 0.1 (wt./wt. or vol./vol.) % $CO_2$ and a composition that generates $CO_2$; and taking a second measurement of the amount of water removed from soil by the plant over a period of time, where the second measurement is reduced relative to the first measurement.

In some embodiments, the method further includes taking a first measurement of the amount of water transpired by a plant over a period of time; providing the plant with a composition that is at least one of a composition comprising at least about 0.1 (wt./wt. or vol./vol.) % $CO_2$ and a composition that generates $CO_2$; and taking a second measurement of the amount of water transpired by the plant over a period of time, where the second measurement is reduced relative to the first measurement.

In this regard, the amount of water consumed by a plant may be reduced from about 5% to about 10%, from about 10% to about 15%, from about 15% to about 20%, from about 20% to about 30%, from about 30% to about 40%, from about 40% to about 50%, from about 50% to about 75%, from about 75% to about 100%, or a range between and including any two of these values, during a period of time of from about one day to about one week, from about one week to about one month, from about six months to about one year, from about one year to about five years, or a range between and including any two of these values. In some embodiments, the plant is grown on a farm, orchard, or in a forest. In some embodiments, the plant is a tree.

According to another aspect, an article is provided where the article includes a plant, and a composition that comprises at least about 0.1 (wt./wt. or vol./vol.) % $CO_2$ or at least about 0.1 wt./wt. % of a composition that generates $CO_2$.

In some embodiments of the article, the composition that generates $CO_2$ includes the reaction product of an amine, or a salt thereof, with $CO_2$. In some embodiments, the composition that generates $CO_2$ includes the reaction product of an amine, or a salt thereof, and $CO_2$. In some embodiments, the amine is ammonia, a primary ($C_6$-$C_{30}$) alkyl amine, piperidine, morpholine, monoethanolamine (MEA), diethanolamine (DEA), methyldiethanolamine (MDEA), diisopropylamine (DIPA), aminoethoxyethanol (DGA), or a combination thereof.

In some embodiments of the article, the composition that generates $CO_2$ includes a $CO_2$-precursor compound, or salt thereof, selected from citric acid, cis-aconitic acid, isocitric acid, oxalosuccinic acid, α-ketoglutaric acid, succinic acid, fumaric acid, malic acid, oxaloacetic acid, and a combination thereof.

In some embodiments of the article, the composition that generates $CO_2$ further includes an enzyme that catalyzes a conversion or decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or decarboxylation of the $CO_2$-precursor compound. In some embodiments, the microorganism is a lactic acid bacterium.

In some embodiments of the article, the composition comprising at least about 0.1 wt./wt. % $CO_2$ is in a condensed phase. In some embodiments, the composition that comprises at least about 0.1 wt./wt. % $CO_2$ is a fluid comprising $CO_2$. In some embodiments, the composition that comprises at least about 0.1 vol./vol. % $CO_2$ is a gas comprising $CO_2$. In some embodiments, the composition comprising at least about 0.1 (wt./wt. or vol.vol.) % $CO_2$ comprises at least about 1.0 (wt./wt. or vol./vol.) % $CO_2$. In some embodiments, the composition comprising at least about 0.1 (wt./wt. or vol.vol.) In some embodiments, the composition further includes water.

In some embodiments of the article, the composition further includes an excipient. In some embodiments, the excipient is selected from a fungicide, antibiotic, antiviral, pesticide, growth regulator, nutrient, anti-herbivore agent, fertilizer, stomata control agent, or a combination thereof. In some embodiments, the composition further includes a stomata control agent. In some embodiments, the stomata control agent includes abscisic acid or a salt or precursor thereof. In some embodiments, the composition is included within a fluid, gel, an aerosol, a solution, or a suspension. In some embodiments, the plant is a tree.

According to another aspect is an apparatus for providing a composition that comprises $CO_2$ or a composition that generates $CO_2$ into a plant, where the apparatus includes the following components: at least one infusion pump for delivering the composition that comprises $CO_2$ or the composition that generates $CO_2$ into the plant; at least one sensor; at least one control unit comprising a microprocessor; at least one user interface, operatively connected to the control unit; and at least one data output interface operatively connected to one or more of the other components.

In some embodiments, the apparatus further includes an extraction pump for extracting carbon-based photosynthate from the plant. In some embodiments, the data output interface is adapted for wireless communication. In some embodiments, the data output interface is adapted for wired communication. In some embodiments, the data output interface is adapted for removal of a physical storage medium. In some embodiments, the control unit coordinates one or more of the other components necessary to monitor multiple plants. In some embodiments, at least one sensor detects suitable location and depth within the plant where the composition can be provided. In some embodiments, at least one sensor detects the rate at which the composition is provided into the plant or the rate at which the carbon-based photosynthate is extracted from the plant. In some embodiments, at least one sensor detects the amount of the composition provided into the plant or the amount of the carbon-based photosynthate extracted from the plant. In some embodiments, the apparatus further includes at least one absorber unit or at least one regenerator unit, each operatively connected to the control unit. In some embodiments, the apparatus further includes a processing unit for processing the carbon-based photosynthate into $CO_2$ and energy and an conversion unit for converting some of the energy into electricity. In some embodiments, the apparatus further includes a fuel cell. In some embodiments, the apparatus further includes a container for storing the $CO_2$ produced from the processed carbon-based photosynthate.

In some embodiments, the rate of transpiration by the plant is reduced over the period of time. In this regard, the rate of transpiration over a period of time, as described herein, may be reduced from about 5% to about 10%, from about 10% to about 25%, from about 25% to about 50%, from about 50% to about 90%, or a range between and including any two of these values, during a period of time of from about one day to about one week, from about one week to about one month, from about six months to about one year, from about one year to about fifty years, or a range between and including any two of these values.

In some embodiments of the apparatus, the composition includes at least about 0.1 (wt./wt. or vol./vol.) % $CO_2$ or at least about 0.1 wt./wt. % of a composition that generates $CO_2$.

In some embodiments of the apparatus, the composition that generates $CO_2$ includes the reaction product of an amine, or a salt thereof, with $CO_2$. In some embodiments, the composition that generates $CO_2$ includes the reaction product of an amine, or a salt thereof, and $CO_2$. In some embodiments, the amine is ammonia, a primary ($C_6$-$C_{30}$) alkyl amine, piperidine, morpholine, monoethanolamine (MEA), diethanolamine (DEA), methyldiethanolamine (MDEA), diisopropylamine (DIPA), aminoethoxyethanol (DGA), or a combination thereof.

In some embodiments of the apparatus, the composition that generates $CO_2$ includes a $CO_2$-precursor compound, or salt thereof, selected from citric acid, cis-aconitic acid, isocitric acid, oxalosuccinic acid, α-ketoglutaric acid, succinic acid, fumaric acid, malic acid, oxaloacetic acid, and a combination thereof.

In some embodiments of the apparatus, the composition that generates $CO_2$ further includes an enzyme that catalyzes a conversion or decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or decarboxylation of the $CO_2$-precursor compound. In some embodiments, the microorganism is a lactic acid bacterium.

Methods and Articles for Sequestering $CO_2$

According to one aspect, a method is provided for sequestering $CO_2$ comprising providing a plant with a composition that is at least one of a composition comprising at least about 0.1 (wt./wt. or vol./vol.) % $CO_2$ or at least about 0.1 wt./wt. % of a composition that generates $CO_2$; removing carbon-based photosynthate from the plant; and storing or processing the carbon-based photosynthate.

In some embodiments, the method further includes sequestering at least a portion of the carbon-based photosynthate in a non-oxidative environment. In some embodiments, the method further includes monitoring the amount of water removed from soil by a plant. In some embodiments, the method further includes adjusting the amount of the composition that is provided to the plant or the amount of carbon-based photosynthate that is removed from the plant. In some embodiments, the rate of transpiration by the plant is reduced over the period of time. In some embodiments, the composition that generates $CO_2$ includes the reaction product of an amine, or a salt thereof, and $CO_2$.

In some embodiments of the method, the composition that generates $CO_2$ includes the reaction product of an amine, or a salt thereof, and $CO_2$. In some embodiments, the amine is ammonia, a primary ($C_6$-$C_{30}$) alkyl amine, piperidine, morpholine, monoethanolamine (MEA), diethanolamine (DEA), methyldiethanolamine (MDEA), diisopropylamine (DIPA), aminoethoxyethanol (DGA), or a combination thereof.

In some embodiments of the method, the composition that generates $CO_2$ comprises a $CO_2$-precursor compound, or salt thereof, selected from citric acid, cis-aconitic acid, isocitric acid, oxalosuccinic acid, α-ketoglutaric acid, succinic acid, fumaric acid, malic acid, oxaloacetic acid, and a combination thereof.

In some embodiments of the method, the composition that generates $CO_2$ further includes an enzyme that catalyzes a conversion or decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or decarboxylation of the $CO_2$-precursor compound. In some embodiments, the microorganism is a lactic acid bacterium.

In some embodiments, the composition includes at least about 0.1 wt./wt. % $CO_2$ is in a condensed phase. In some embodiments, the composition that includes at least about 0.1 wt./wt. % $CO_2$ is a fluid comprising $CO_2$. In some embodiments, the composition that includes at least about 0.1 vol./vol. % $CO_2$ is a gas comprising $CO_2$. In some embodiments, the composition including at least about 0.1 (wt./wt. or vol.vol.) % $CO_2$ includes at least about 1.0 (wt./wt. or vol./vol.) % $CO_2$. In some embodiments, the composition including at least about 0.1 (wt./wt. or vol.vol.) % $CO_2$ includes at least about 10.0 (wt./wt. or vol./vol.) % $CO_2$.

In some embodiments, the composition further includes water. In some embodiments, the method further includes monitoring the amount of water transpired from a plant. In some embodiments, the composition further includes an excipient. In some embodiments, the excipient is selected from a fungicide, antibiotic, antiviral, pesticide, growth regulator, nutrient, anti-herbivore agent, fertilizer, stomata control agent and a combination thereof. In some embodiments, the composition is a fluid, gel, or a suspension.

In some embodiments, the composition is provided into the vasculature system of the plant or to the immediate proximity thereof. In some embodiments, the composition is provided into the phloem or xylem of the plant or to the immediate proximity thereof. In some embodiments, the composition is provided to the plant by injecting the composition into the plant. In some embodiments, the composition is provided to a leaf or root of the plant or to the immediate proximity thereof. In some embodiments, some of the cells of the native vascular system of the tree have been removed and replaced with a functional substitute.

In some embodiments, the carbon-based photosynthate is extracted from the phloem or xylem of the plant or from the immediate proximity thereof. In some embodiments, the carbon-based photosynthate includes a carbohydrate.

In some embodiments, the method further includes increasing the quantity of the carbon-based photosynthate that is produced by the plant during an interval of time. In some embodiments, the interval of time is at least one week and the quantity is increased by at least 10%. In other embodiments, the method further includes monitoring the quantity of the carbon-based photosynthate that is produced by a plant during an interval of time. In some embodiments, the method further includes correlating the quantity of the carbon-based photosynthate that is produced by a plant with the amount of composition provided to the plant.

In some embodiments, the method further includes increasing the rate of translocation by a plant during an interval of time. In some embodiments, the interval of time is at least one week and the rate of translocation is increased by at least 10%.

In some embodiments, the method further includes reducing the rate of absorption of atmospheric $CO_2$ by the plant during an interval of time. In some embodiments, the interval of time is at least one week and the rate of absorption of atmospheric $CO_2$ is decreased by at least 10%.

In some embodiments, the carbon-based photosynthate includes carbon derived in part from the composition. In some embodiments, the method is at least partially automated. In some embodiments, the composition is provided under positive pressure up to about 1,000 pounds per square inch (7 MPa).

In some embodiments, the stored carbon-based photosynthate is substantially prevented from contacting oxygen. In some embodiments, the stored carbon-based photosynthate is substantially prevented from being oxidized. In some embodiments, the carbon-based photosynthate is stored in a container or compartment. In some embodiments, the carbon-based photosynthate is stored in a flexible container, such as a plastic bag. In some embodiments, the carbon-based photosynthate is stored in a drum. In some embodiments, the carbon-based photosynthate is stored underground. In some embodiments, the carbon-based photosynthate is buried.

In some embodiments, the plant is a wild-type plant or is a domesticated plant. In some embodiments, the plant has been genetically engineered. In some embodiments, the plant has been bred or genetically engineered to consume a reduced amount of soil-derived water over an interval of time relative to a corresponding wild-type plant. In some embodiments, the plant has been bred or genetically engineered to produce a greater quantity of carbon-based photosynthate over an interval of time relative to a corresponding wild-type plant. In some embodiments, the plant has been bred or genetically engineered to have fewer stomata relative to the wild-type plant. In some embodiments, the plant is grown on a farm, orchard, or in a forest. In some embodiments, the plant is a tree. In some embodiments, the tree is a hardwood selected from an alder, ash, aspen, balsa, beech, birch, cherry, chestnut, cottonwood, dogwood, elm, eucalyptus, gum, hickory, mahogany, maple, oak, poplar, walnut, and willow. In some embodiments, the tree is a softwood selected from a cedar, cypress, fir, yew, hemlock, pine, and spruce.

Methods and Articles for Generating Electricity and Producing Materials

According to one aspect, a method is provided for producing electricity comprising: providing a composition, that is at least one of a composition comprising at least about 0.1 (wt./wt. or vol./vol.) % $CO_2$ or at least about 0.1 wt./wt. % of a composition that generates $CO_2$, to a plant; removing a carbon-based photosynthate from the plant; processing at least a fraction of the carbon-based photosynthate to produce energy and a product stream; and converting at least some of the energy into electricity. In some embodiments, the method further includes capturing at least a portion of the $CO_2$ produced upon processing (e.g., combustion) and providing the captured $CO_2$ into one or more plants.

During the process of photosynthesis, plants such as trees, fix $CO_2$ into carbon-based photosynthate (e.g., sugars, lipids, proteins, primary or secondary metabolites). This reductive process stores, as carbon-based photosynthate, many megawatts of chemical energy per $km^2$. The compositions and methods described herein can be used to optimize production and facilitate harvesting of the carbon-based photosynthate. Once harvested, the carbon-based photosynthate can be oxidized, e.g., via combustion or within a fuel cell (e.g., SOFC), to recover at least some of the energy stored therein. In some embodiments, the carbon-based photosynthate that is extracted from the plant can be added to fuel cells to efficiently convert the extracted components into energy. In some embodiments, the fuel cells include glucose oxidase. Alternatively, the carbon-based photosynthate that is extracted from the plant can be used as a feedstock to prepare any conceivable carbon-based food or beverage, or as a feedstock to manufacture any conceivable carbon-based specialty material or fuel.

In some embodiments, the carbon-based photosynthate, from which electricity or materials are generated, can be extracted from the plant at any time during the year. One of the advantages of the methods of using $CO_2$ or a composition that generates $CO_2$ is that plants, such as trees, can be harvested of photosynthate at any time during the year. Harvest need not be constrained to a particular growing season. For example, the methods described herein can be used to minimize the amount of carbon-based photosynthate that is oxidized by the tree as a result of autophagic flux. Autophagic flux is a catabolic process involving the degradation of a cell's or an organism's own components. For example, some plants cannibalize their own carbon-based photosynthate, stored within leaves, before such leaves are shed from the plant in autumn.

The compositions and methods described herein can be used to continually stimulate plants, by the addition of $CO_2$ or composition that generates $CO_2$, to produce carbon-based photosynthate that, in turn, can be harvested year-round, rather than being catabolized by the tree as a result of autophagic flux. Further, the added $CO_2$ or composition that generates $CO_2$, can be supplemented with one or more excipients that modulate plant growth (e.g., antivirals or any agent to accelerate or retard root growth).

The harvest of carbon-based photosynthate from the plant may optionally include extracting or refining steps to concentrate the carbon-based photosynthate of interest from the remaining solution which is substantially free of carbon-based photosynthate. The remaining solution which is substantially free of carbon-based photosynthate can optionally be added back to the plant.

In some embodiments, the volume or mass of carbon-based photosynthate that are extracted from the plant or from a number of plants within an area can be tabulated and, optionally, monitored to obtain carbon credits, in exchange for the amount of $CO_2$ that is provided into plants, such as trees, where one carbon credit is equal to one metric ton of carbon dioxide. "Carbon credit" is a generic term for any tradable certificate or permit representing the right to emit one ton of carbon dioxide or the mass of another greenhouse gas with a carbon dioxide equivalent ($tCO_2e$) equivalent to one ton of carbon dioxide.

In some embodiments, the method further includes correlating the amount of electricity produced with the amount of the compound provided to the plant. In some embodiments, the method includes using a fuel cell to process at least a fraction of the carbon-based photosynthate to produce electrical energy and a product stream. In some embodiments, the method includes using combustion to process at least a fraction of the carbon-based photosynthate to produce thermal energy and a product stream. In some embodiments, the method further includes providing at last a fraction of the product stream to the plant. In some embodiments, providing at last a fraction of the product stream to the plant includes processing at least a portion of the product stream into the composition. In some embodiments, the method further includes monitoring the amount of water removed from soil by a plant. In some embodiments, the method further includes adjusting the amount of the composition that is provided to the plant or the amount of carbon-based photosynthate that is removed from the plant. In some embodiments, the rate of transpiration by the plant is reduced over a period of time.

In some embodiments, the composition comprising at least about 0.1 wt./wt. % $CO_2$ is in a condensed phase (e.g., under >1 atmosphere of pressure or dissolved in a fluid). In some embodiments, the composition that includes at least about 0.1 wt./wt. % $CO_2$ is a fluid comprising $CO_2$. In some embodiments, the composition that includes at least about 0.1 vol./vol. % $CO_2$ is a gas comprising $CO_2$. In some embodiments, the composition comprising at least about 0.1 (wt./wt. or vol.vol.) % $CO_2$ includes at least about 1.0 (wt./wt. or vol./vol.) % $CO_2$. In some embodiments, the composition comprising at least about 0.1 (wt./wt. or vol.vol.) % $CO_2$ includes at least about 10.0 (wt./wt. or vol./vol.) % $CO_2$.

In some embodiments of the method, the composition that generates $CO_2$ includes the reaction product of an amine, or a salt thereof, and $CO_2$. In some embodiments, the amine is ammonia, a primary ($C_6$-$C_{30}$) alkyl amine, piperidine, morpholine, monoethanolamine (MEA), diethanolamine (DEA), methyldiethanolamine (MDEA), diisopropylamine (DIPA), aminoethoxyethanol (DGA), or a combination thereof.

In some embodiments of the method, the composition that generates $CO_2$ includes a $CO_2$-precursor compound, or salt thereof, selected from citric acid, cis-aconitic acid, isocitric acid, oxalosuccinic acid, α-ketoglutaric acid, succinic acid, fumaric acid, malic acid, oxaloacetic acid, and a combination thereof.

In some embodiments of the method, the composition that generates $CO_2$ further includes an enzyme that catalyzes a conversion or decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or decarboxylation of the $CO_2$-precursor compound. In some embodiments, the microorganism is a lactic acid bacterium.

In some embodiments, the composition that generates $CO_2$ further includes an enzyme that catalyzes a conversion or a decarboxylation of the $CO_2$-precursor compound. In some embodiments, the enzyme is malate dehydrogenase, NAD-malic enzyme, or a combination thereof. In some embodiments, the composition that generates $CO_2$ further includes a microorganism or fraction thereof having an enzyme that catalyzes a conversion or a decarboxylation of the $CO_2$-precursor compound. In some embodiments, the microorganism is a lactic acid bacterium.

In some embodiments, the composition further includes water. In some embodiments, the method further includes monitoring the amount of water transpired from a plant. In some embodiments, the composition further includes an excipient. In some embodiments, the excipient is selected from a fungicide, antibiotic, antiviral, pesticide, growth regulator, nutrient, anti-herbivore agent, fertilizer, stomata control agent and a combination thereof. In some embodiments, the composition is a fluid, gel, or a suspension.

In some embodiments, the composition is provided into the vasculature system of the plant or to the immediate proximity thereof. In some embodiments, the composition is provided into the phloem or xylem of the plant or to the immediate proximity thereof. In some embodiments, the composition is provided to the plant by injecting the composition into the plant. In some embodiments, the composition is provided to a leaf or root of the plant or to the immediate proximity thereof. In some embodiments, some of the cells of the native vascular system of the tree have been removed and replaced with a functional substitute.

In some embodiments, the carbon-based photosynthate is extracted from the phloem or xylem of the plant or from the immediate proximity thereof. In some embodiments, the carbon-based photosynthate includes a carbohydrate.

In some embodiments, the method further includes increasing the quantity of the carbon-based photosynthate that is produced by the plant during an interval of time. In some embodiments, the interval of time is at least one week and the quantity is increased by at least 10%. In other embodiments, the method further includes monitoring the quantity of the carbon-based photosynthate that is produced by a plant during an interval of time. In some embodiments, the method further includes correlating the quantity of the carbon-based photosynthate that is produced by a plant with the amount of composition provided to the plant.

In some embodiments, the method further includes increasing the rate of translocation by a plant during an interval of time. In some embodiments, the interval of time is at least one week and the rate of translocation is increased by at least 10%.

In some embodiments, the method further includes reducing the rate of absorption of atmospheric $CO_2$ by the plant during an interval of time. In some embodiments, the interval of time is at least one week and the rate of absorption of atmospheric $CO_2$ is decreased by at least 10%.

In some embodiments, the carbon-based photosynthate includes carbon derived in part from the composition. In some embodiments, the method is at least partially automated. In some embodiments, the composition is provided under positive pressure up to about 1,000 pounds per square inch (7 MPa).

In some embodiments, the plant is a wild-type plant or is a domesticated plant. In some embodiments, the plant has been genetically engineered. In some embodiments, the plant has been bred or genetically engineered to consume a reduced amount of soil-derived water over an interval of time relative to a corresponding wild-type plant. In some embodiments, the plant has been bred or genetically engineered to produce a greater quantity of carbon-based photosynthate over an interval of time relative to a corresponding wild-type plant. In some embodiments, the plant has been bred or genetically engineered to have fewer stomata relative to the wild-type plant.

In some embodiments, the plant is grown on a farm, orchard, or in a forest. In some embodiments, the plant is a tree. In some embodiments, the tree is a hardwood selected from an alder, ash, aspen, balsa, beech, birch, cherry, chestnut, cottonwood, dogwood, elm, eucalyptus, gum, hickory, mahogany, maple, oak, poplar, walnut, and willow. In some embodiments, the tree is a softwood selected from a cedar, cypress, fir, yew, hemlock, pine, and spruce.

According to an additional aspect, the present technology provides an article including a composition including $CO_2$ and/or a composition that generates $CO_2$; and an apparatus for providing the composition into one or more plants; a carbon-based photosynthate that is produced by the one or more plants; and an apparatus for extracting the carbon-based photosynthate; and an apparatus for converting the carbon-based photosynthate into $CO_2$, for example, and heat; and an apparatus for converting some of the heat of combustion into electricity (e.g., solid oxide fuel cell (SOFC) or heat engine). In some embodiments, the apparatus converts the carbon-based photosynthate into $CO_2$ via combustion. In some embodiments, the apparatus converts the carbon-based photosynthate into $CO_2$ via a fuel cell, such as a SOFC.

In some embodiments, the article further includes an apparatus for containing or recirculating the $CO_2$ produced by the combustion of the carbon-based photosynthate. In some embodiments, the article further includes an apparatus for providing the contained $CO_2$ into one or more plants.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following Examples, which are provided by way of illustration and are not intended to be limiting of the present technology.

EXAMPLES

Example 1: Measuring the Rate of Transpiration of Trees

Six potted trees A, B, C, D, E and F of approximately the same height and weight and having approximately the same number of leaves are grown in a fixed quantity of soil having the same approximate composition. The tops of the pots are sealed with plastic around the base of each tree to minimize the evaporation of water from the soil. The potted trees are set on scales and watered in the evening at identical times with identical quantities of water. The weight of each potted tree are continuously monitored for one week to determine how much water transpires from each tree, per hour, during the day. During the second week, trees A-F are continually watered as during the first week. Additionally, during the second week, the xylem of trees A-E is provided with water or an aqueous composition as follows: The xylem of tree A is provided with an aqueous composition including $CO_2$ gas. The xylem of tree B is provided with an aqueous composition of malic acid, a $CO_2$-precursor compound. The xylem of tree C is provided with an aqueous composition of malic acid, malate dehydrogenase, and NAD-malic enzyme. The xylem of tree D is provided with an aqueous composition of diethanolamine/$CO_2$. The xylem of tree E is provided with water. The xylem of tree F is not provided with water or any of the above-described compositions.

After two weeks, the weight loss attributable to transpiration (in kilograms of water per hour) for each tree A-F is compared. It is contemplated that during the second week the water-based weight loss for some or all of trees A-D will be reduced relative to trees E and F.

Thus, the injection of a composition including $CO_2$ or a $CO_2$-precursor compound is contemplated to decrease the rate of transpiration and thus reduce the mass of water lost by trees A-D relative to control trees E and F.

Example 2: The Incorporation of $^{13}$Carbon into Tree Sap by Providing into Trees a Composition Including $^{13}CO_2$ or a Composition that Generates $^{13}CO_2$ Six potted trees, A-F, as described in Example 1, are watered for one week. During the second week, trees A-F are continually watered as during the first week. Additionally, during the second week, the xylem of trees A-E is provided with water or an aqueous composition as follows: The xylem of tree A is provided with an aqueous composition including $^{13}CO_2$ gas. The xylem of tree B is provided with an aqueous composition of $^{13}$C-malic acid, a $^{13}CO_2$-precursor compound. The xylem of tree C is provided with an aqueous composition of $^{13}$C-malic acid, malate dehydrogenase, and NAD-malic enzyme. The xylem of tree D is provided with an aqueous composition of diethanolamine/$^{13}CO_2$. The xylem of tree E is provided with water. The xylem of tree F is not provided with water or any of the above-described compositions.

During the second week, one gram of sap per day is collected from each of trees A-F by placing a tap into the phloem of each tree. Liquid chromatography mass spectrometry (LCMS) and $^{13}$C-nuclear magnetic resonance (NMR) spectroscopy can be used to determine whether an increased quantity of $^{13}$C incorporates into the carbohydrate components of sap obtained from trees A-D relative to the control trees E and F.

Example 3: The Sequestration of Tree Sap Having $^{13}$C-Enriched Carbohydrates from the Injection of a Composition Including $^{13}CO_2$ or a Composition that Generates $^{13}CO_2$ into Trees The procedure of Example 2 is continued until ten grams of sap is collected from each of trees A-F. Each sap sample is then sealed in a plastic (polyethylene) bag. During subsequent months and years, LCMS and $^{13}$C-NMR analysis can be used to confirm that the concentration of carbohydrate components and the levels of incorporation of $^{13}$C into the carbohydrate components remain constant. Thus, $^{13}CO_2$ from a composition including $^{13}CO_2$ or a composition that generates $^{13}CO_2$ can be sequestered after being provided into trees, converted to sap, collected and stored to exclude oxygen.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed:

1. A method for reducing an amount of water removed from soil by a plant through transpiration over an interval of time, the method comprising providing a composition that generates $CO_2$ to the xylem of the plant;
   wherein the composition that generates $CO_2$ comprises a reaction product of an amine, or salt thereof, with $CO_2$;
   wherein the amine, or a salt thereof, is selected from the group consisting of ammonia, a primary $C_6$-$C_{30}$ alkyl amine, piperidine, morpholine, monoethanolamine (MEA), diethanolamine (DEA), methyldiethanolamine (MDEA), diisopropylamine (DIPA), aminoethoxyethanol (DGA), and a combination of any two or more thereof;
   growing the plant under conditions which allow the plant to produce a carbon-based photosynthate, wherein the carbon-based photosynthate comprises carbon derived in part from the composition provided to the plant; and
   extracting the carbon-based photosynthate from the plant.

2. The method of claim 1, wherein the method further comprises monitoring the amount of water transpired from the plant.

3. The method of claim 2, further comprising correlating the amount of water transpired by the plant with the amount of the composition provided to the plant.

4. The method of claim 1, wherein the method further comprises monitoring the amount of water removed from soil by the plant.

5. The method of claim 4, further comprising correlating the amount of water removed from soil by the plant with the amount of the composition provided to the plant.

6. The method of claim 1, wherein the method further comprises adjusting an amount of the composition that is provided to the plant or the amount of carbon-based photosynthate that is extracted from the plant.

7. The method of claim 6, wherein the adjustment is based upon the amount of water removed from soil by the plant.

8. The method of claim 6, wherein the adjustment is based upon the amount of water transpired by the plant.

9. The method of claim 1, wherein a rate of transpiration by the plant is reduced over the interval of time.

10. The method of claim 1, wherein the composition further comprises a $CO_2$-precursor compound, or salt thereof;
    wherein the $CO_2$-precursor compound, or salt thereof is citric acid, cis-aconitic acid, isocitric acid, oxalosuccinic acid, α-ketoglutaric acid, succinic acid, fumaric acid, malic acid, oxaloacetic acid, or a combination of any two or more thereof.

11. The method of claim 1, wherein the composition further comprises a stomata control agent.

12. The method of claim 1, wherein the composition is a fluid, a gel, an aerosol, a solution, or a suspension.

13. The method of claim 1, wherein the composition is provided to the plant by injecting the composition into the plant.

14. The method of claim 1, further comprising increasing an amount of the carbon-based photosynthate that is extracted from the plant during the interval of time.

15. The method of claim 1, wherein the method is at least partially automated.

16. The method of claim 1, wherein the plant is a tree.

17. The method of claim 1, further comprising
    taking a first measurement of the amount of water removed from soil by the plant through transpiration over the interval of time;
    providing the plant with the composition and
    taking a second measurement of the amount of water removed from soil by the plant over the interval of time, wherein the second measurement is reduced relative to the first measurement.

18. The method of claim 1, further comprising
    taking a first measurement of the amount of water transpired by the plant through transpiration over the interval of time;
    providing the plant with the composition; and
    taking a second measurement of the amount of water transpired by the plant over the interval of time, wherein the second measurement is reduced relative to the first measurement.

19. The method of claim 1, wherein the extracting comprises extracting the carbon-based photosynthate in a fluid form without any external cutting.

20. The method of claim 1, wherein the extracting comprises transportation via a conduit.

21. The method of claim 20, wherein the conduit is a flow line, pipe, tube, or hose.

22. The method of claim 21, wherein the conduit is attached to an apparatus for extracting or storing the carbon-based photosynthate.

23. The method of claim 22, wherein the apparatus includes an extraction pump.

* * * * *